(12) United States Patent
Galarza et al.

(10) Patent No.: US 7,556,940 B2
(45) Date of Patent: Jul. 7, 2009

(54) ASSEMBLY OF WILD-TYPE AND CHIMERIC INFLUENZA VIRUS-LIKE PARTICLES (VLPS)

(75) Inventors: Jose M. Galarza, Hartsdale, NY (US); Theresa E. Latham, Mamaroneck, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 210 days.

(21) Appl. No.: 11/091,309

(22) Filed: Mar. 28, 2005

(65) Prior Publication Data

US 2005/0186621 A1 Aug. 25, 2005

Related U.S. Application Data

(63) Continuation of application No. 10/311,580, filed as application No. PCT/US01/19890 on Jun. 21, 2001, now abandoned.

(60) Provisional application No. 60/213,656, filed on Jun. 23, 2000, provisional application No. 60/284,411, filed on Apr. 17, 2001.

(51) Int. Cl.
*C12P 21/00* (2006.01)
*C12N 15/00* (2006.01)
*C12N 15/09* (2006.01)
*C12N 15/44* (2006.01)
*C12N 15/47* (2006.01)
*C12N 7/00* (2006.01)
*C12N 7/02* (2006.01)
*C12N 7/04* (2006.01)
*A61K 39/00* (2006.01)
*A61K 39/145* (2006.01)
*A61K 39/205* (2006.01)
*C07H 21/00* (2006.01)

(52) U.S. Cl. .............. 435/69.3; 435/69.1; 435/69.7; 435/235.1; 435/236; 435/239; 435/320.1; 536/23.4; 536/23.72; 424/184.1; 424/192.1; 424/204.1; 424/209.1

(58) Field of Classification Search .............. None
See application file for complete search history.

(56) References Cited

U.S. PATENT DOCUMENTS

| 4,009,258 A * | 2/1977 | Kilbourne ............ 424/206.1 |
| 4,666,829 A | 5/1987 | Glenner et al. |
| 5,298,244 A | 3/1994 | Redmond et al. |
| 5,830,877 A | 11/1998 | Carson et al. |
| 6,001,634 A * | 12/1999 | Palese et al. ............ 435/235.1 |
| 6,207,646 B1 | 3/2001 | Krieg et al. |

FOREIGN PATENT DOCUMENTS

| WO | WO 99/27944 | 6/1999 |
| WO | WO 99/51259 | 10/1999 |
| WO | WO 00/18434 | 4/2000 |
| WO | WO 00/60050 | 10/2000 |

OTHER PUBLICATIONS

Chen et al., "Influenza virus hemagglutinin and neuraminidase, but not the matrix protein, are required for assembly and budding of plasmid-derived virus-like particles," Journal of Virology, vol. 81 No. 13, pp. 7111-7123 (Jul. 2007).*
Johansson et al., Virology, vol. 225 No. 1, pp. 136-144 (Nov. 1996).*
McQueen et al., Proceedings of the National Acadamy of Sciences, vol. 83, pp. 9318-9322 (Dec. 1986).*
McQueen et al., Journal of Biological Chemistry, vol. 262, No. 33, pp. 16233-16240 (1987).*
McQueen et al., Proceedings of the National Acadamy of Sciences, vol. 81, pp. 395-399 (Jan. 1984).*
Yilma et al., Advances in Experimental Medicine and Biology, vol. 185, pp. 101-115 (1985).*
Lamb, R.A., The Influenza Viruses, pp. 1-87, R.M. Krug, ed. (Plenum Press, 1989).
Lamb, R.A. et al., Cell 40:627-633 (1985).
Martin, K. and Helenius, A., Cell 67:117-130 (1991).
Shapiro, G.I. et al., J Virol 61:764-773 (1987).
Garoff, H. et al., Microbiology and Molecular Biology Reviews 62:1171-1190 (1998).
Nayak, D.P., ASM News 62:411-414 (1996).
Justice, P.A. et al., J Virol 69:3156-3160 (1995).
Li, Y. et al., J Virol 67:4415-4420 (1993).
Mebatsion, T. et al., Cell 84:941-951 (1996).
Coronel, E.C. et al., J Virol 73:7035-7038 (1999).
Zhao, H. et al., J Gen Virol 79:2435-2446 (1998).
Jin, H., EMBO J 13:5504-5515 (1994).
Jin, H. et al., EMBO J 16:1236-1247 (1997).
Zhang, J. et al., J Virol 74:4634-4644 (2000).
Ruigrok, R.W.H. et al., Virology 267:289-298 (2000).
Roberts, P.C. et al., Virology 240:127-137 (1998).
Kirnbauer, R. et al., Proc Natl Acad Sci USA 89:12180-12184 (1992).
Loudon, P.T. and Roy, P., Virology 180:798-802 (1991).
Rose, R.C. et al., J Virol 67:1936-1944 (1993).
Zeng, C.Q.-Y. et al., J Virol 70:2736-2742 (1996).
Gheysen, D. et al., Cell 59:103-112 (1989).
Nermut, M.V. et al., Virology 198:288-296 (1994).
Takahaski, H. et al., Virology 256:371-380 (1999).
Yamshchikov, G.V. et al., Virology 214:50-58 (1995).
Ford, T. et al., Analytical Biochem 220:360-366 (1994).

(Continued)

*Primary Examiner*—Zachariah Lucas
(74) *Attorney, Agent, or Firm*—Alan M. Gordon

(57) ABSTRACT

Influenza virus-like particles (VLPs) comprising the structural proteins HA, NA, M1 and M2 are described. VLPs are also generated containing M1 alone, as are VLPs with M1 and any one or two of HA, NA and M2. VLPs with HA from one influenza subtype and NA from a different influenza subtype are also described, as are VLPs in which a portion or all of HA or NA is replaced by a heterologous moiety not produced by influenza virus, so as to comprise chimeric VLPs.

**7 Cla

OTHER PUBLICATIONS

Galarza, J.M. et al., Virus Res 24:91-106 (1992).
Gomez-Puertas, P. et al., J Gen Virol 80:1635-1645 (1999).
Neumann, G. et al., J Virol 74:547-551 (2000).
Gomez-Puertas, P. et al., J Virol 74:11538-11547 (2000).
Bui, M. et al., J Virol 74:1781-1786 (2000).
Cadd, T.L. et al., BioEssays 19:993-1000 (1997).

* cited by examiner

VSV-G/HA CHIMERA GENE

...GETLFFGDTGLSKNPIEFVEGWFSSWKSKSGYKDWILWISFAISCFLLCVVLLGFIMWACQKGNIRCNICI

| 418 aa | 29 aa | 14 aa |
|---|---|---|
| VSV-G ECTODOMAIN | FLU HA TRANSMEMBRANE DOMAIN | FLU HA CYTOPLASMIC TAIL |

FIG. 2

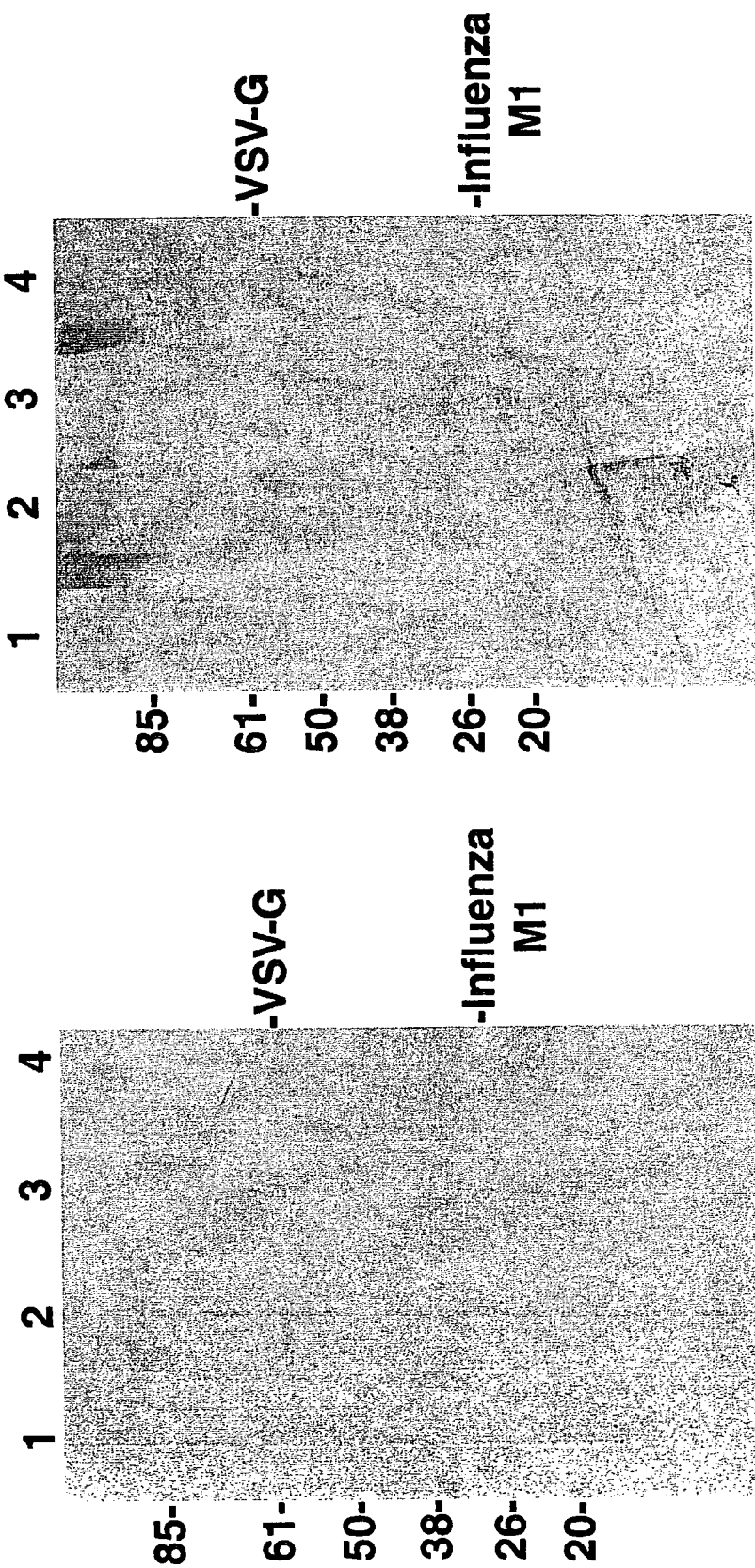

FIG.14

Quadruple transfer vector carrying the three polymerase subunits and nucleocapsid NP of influenza virus Labels: EcoRI, ColE ori, Amp R, EcoRI, HindIII, HindIII, SnaBI, SacI, NheI, SpeI, PB1 gene, pH promoter, p10 promoter, PB2 gene, pH promoter, PA gene, NotI, NotI, PmeI, p10 promoter, NP gene, BglII, EcoRI, NaeI Expression of GFP in BHK cells following infection with VLPs carrying the GFP gene (arrows indicate expressing cells)

ASSEMBLY OF WILD-TYPE AND CHIMERIC INFLUENZA VIRUS-LIKE PARTICLES (VLPS)

CROSS-REFERENCE TO RELATED APPLICATIONS

The present application is a continuation application of U.S. application Ser. No. 10/311,580, filed on Dec. 16, 2002, now abandoned which is the national stage application of and claims the benefit of International Application No. PCT/US01/19890, filed on Jun. 21, 2001, which claims the benefit of U.S. Provisional Application No. 60/213,656, filed on Jun. 23, 2000, and U.S. Provisional Application No. 60/284,411, filed on Apr. 17, 2001.

FIELD OF THE INVENTION

This invention relates to influenza virus-like particles composed of the matrix protein alone, and may further include any of the structural proteins of influenza.

BACKGROUND OF THE INVENTION

The influenza viruses consist of subtypes designated A, B and C. Influenza viruses possess a segmented, single negative strand RNA genome which encodes 10 polypeptides that are required for the life cycle of the virus. Each of the eight RNA segments of a complete genome is encapsidated with multiple subunits of the nucleocapsid protein (NP) and associated with a few molecules of the trimeric polymerase (PB1, PB2 and PA subunits), thereby forming the ribonucleoprotein complex (RNP) (Bibliography entry 1). Surrounding these structures is a layer of the matrix protein (M1), which appears to serve as a nexus between the core and the viral envelope. This host cell-derived envelope is studded with the two major virally encoded surface glycoproteins hemagglutinin (HA) and neuraminidase (NA), and a much smaller amount of a nonglycosylated small protein M2 (1,2). The HA glycoprotein is cleaved by a protease to form HA1 and HA2.

Influenza viral infection is initiated by the attachment of the surface hemagglutinin to a sialic acid-containing cellular receptor. This first virus-cell interaction induces the uptake of the viral particle into the cell by receptor-mediated endocytosis. Under the low pH conditions of the endosome, the HA undergoes a conformational change that facilitates the interaction of the hydrophobic $NH_2$ terminal domain of HA2 and the endosomal membrane, resulting in membrane fusion and subsequent release of the core RNPs and matrix protein (M1) into the cytosol. Disassociation of the RNPs and matrix proteins occurs in the cytosol before the RNPs are translocated to the nucleus where transcription and replication of the complete genome take place (3,4).

Following primary transcription, newly synthesized proteins initiate the replication of the viral genome which in turn increases transcription and protein synthesis. At this point of the virus life cycle, the surface glycoproteins HA and NA start to accumulate at discrete areas of the plasma membrane from where newly assembled virus will be released. Virus assembly is assumed to begin via some sort of interaction between the cytoplasmic and/or transmembrane domains of the membrane anchored proteins and the underlying matrix protein (M1), which in turn maintains a close association with the RNPs (5,6). Collectively, HA, NA, M1 and M2 constitute the four virally encoded structural proteins. The contacts between matrix protein M1 and the RNP complexes, as well as the mechanism by which a complete set of eight RNPs gets incorporated into the mature virion particle, have not been well defined. Specific molecular contacts among the structural components are assumed to dictate how the process of morphogenesis initiates and progresses to the point of mature particle assembly and budding from the surface of the host cell.

The complexity of the process has given rise to issues such as: 1) The identification of which viral proteins are required for assembly and budding. 2) The type of protein-protein and lipid-protein interactions between the surface and underlying components which drive the assembly and budding process. 3) The mechanisms by which the RNPs are brought into the assembly site, incorporated into the particle and sorted out from analogous segments. 4) The nature and stoichiometry of the interactions and the regulation of assembly and budding. All of these events occur in a complex cellular environment where some host molecules may or may not enhance or interfere with the progression of the assembly and budding process. This, in turn, leads to the issues of whether cellular proteins are indeed involved in viral assembly and how non-viral proteins are generally excluded from the surface of the budded particles.

A large number of studies have been conducted to address some of these issues with enveloped RNA viruses of different families (5); however most of these issues remain unresolved with respect to influenza virus. Studies with non-segmented RNA virus families (such as the Rhabdoviridae and Paramyxoviridae), which are somewhat morphologically and evolutionarily related to influenza, have shown that the matrix protein (M) of the Rhabdovirus Vesicular stomatitis virus (VSV) by itself is capable of pinching off (budding) from the cell surface as membrane particles (7,8). In addition, the importance of M proteins in budding is also reflected in the fact that copies of rabies viruses (another Rhabdovirus) with a deletion of the gene encoding the G surface protein are still formed and released from the infected cells (9). More recent work with PIV-3 (a Paramyxovirus) has also shown that the matrix proteins together with nucleocapsid protein (NP) are able to associate into a virus-like structure and bud from the cell surface (10). With respect to influenza virus however, expression of these two proteins using Semliki Forest virus replicons did not show either association between these proteins or budding of membrane vesicles (11).

Performing reverse genetics of influenza virus has been a useful approach to investigate protein-protein interactions between structural components. The importance of the cytoplasmic domain of the glycoproteins in the assembly of influenza has been recently studied (12,13,14), and it has been shown that deletion of the HA tail reduced its incorporation into the particle as well as the efficiency of budding, but did not affect virion morphology. On the other hand, virus with a deleted NA tail showed a filamentous morphology and the incorporation of NA into the envelope was impaired. In addition, double deletions seemed to decrease the efficiency of budding as well as infectivity and changed virion morphology, which was distinguishable from those with tail deletions and from wild-type virus. Although double tail deletions appeared to affect the efficiency of budding and morphology of the virus particles, they did not completely abrogate assembly and exit of virion particles. This suggested that M1 protein is able to direct viral assembly and budding (13).

Similarly, the interactions established between the matrix protein and the plasma membrane seem to be critical for virus assembly and release. However the physical nature of this association, whether the matrix protein is completely embedded into the plasma membrane or merely attached by electrostatic interaction, is an unresolved issue. A recent work addressing this question strongly suggested that matrix and membrane were associated through electrostatic interactions, but it could not be ruled out that a certain amount of M1 may be embedded into the membrane (15). The key role of M1 and M2 proteins in the structure of the mature virion is reflected in the spherical or filamentous morphology of the particles when amino acid substitutions are present in either of these molecules (16).

Virus-like particles (VLPs) have been the subject of much interest in recent years as potential candidates for inclusion in immunogenic compositions. This is because VLPs contain one or more surface proteins displayed in a conformation similar enough to their native conformation so that they can elicit a desired immune response. At the same time, VLPs lack the complement of the genetic material required to produce viral progeny in a host. Therefore, unlike a wild-type virus, VLPs cannot cause an infection with disease symptoms or pathology. For example, two or three proteins of rotavirus (a double stranded RNA virus) have been assembled into VLPs which elicited an immune response (17).

Baculovirus expression systems have been broadly used to investigate morphogenesis and assembly of VLPs of non-enveloped viruses that self-assemble into icosahedral structures (18,19,20,21). Similarly, expression in insect cells of the proteins gag and/or env of different members of the retrovirus family has also been used to study assembly and budding of the core structure of enveloped viruses (22,23,24,25).

There is a need to assess the ability of the baculovirus expression system to produce influenza VLPs. In particular, there is a need to identify the minimal number of influenza virus proteins which will assemble into VLPs and to evaluate the morphology and immunogenicity of those VLPs.

SUMMARY OF THE INVENTION

Accordingly, it is an object of this invention to identify the minimal number of influenza virus proteins which will assemble into a VLP. It is a further object of this invention to generate VLPs containing proteins from more than one subtype of influenza virus. It is a still further object of this invention to generate chimeric VLPs containing a protein from a heterologous, non-influenza source. It is yet another object of this invention to formulate immunogenic and pharmaceutical compositions containing one or more of the aforementioned VLPs.

These and other objects of the invention as discussed below are achieved by the assembly of influenza VLPs comprising at least one influenza virus structural protein, where said VLPs always include M1. In one embodiment of the invention, the VLPs contain only M1 (which may incorporate the nucleocapsid protein (NP)). Such VLPs are produced by constructing a recombinant DNA molecule which encodes M1, transfecting, infecting or otherwise transforming a suitable host cell with said recombinant DNA molecule, culturing the host cell under conditions which permit the expression of M1, so that VLPs are assembled within the cells after expression of M1, and purifying the VLPs from the culture supernatant.

In another embodiment of the invention, the VLPs further comprise at least one of the influenza structural proteins selected from the group consisting of HA, NA and M2. Such VLPs are produced by constructing one or more recombinant DNA molecules which encode M1 plus at least one of HA, NA and M2, transfecting, infecting or otherwise transforming a suitable host cell with said one or more recombinant DNA molecules, culturing the host cell under conditions which permit the expression of said influenza virus structural proteins, so that VLPs are assembled within the cells after expression of the structural proteins, and purifying the VLPs from the culture supernatant. The VLPs containing M1 only or M1 plus at least one of HA, NA and M2 are formulated with a diluent or carrier as an immunogenic composition for immunizing vertebrates against infection caused by influenza virus.

In still another embodiment of the invention, it may be desirable to produce VLPs containing surface glycoproteins from different subtypes of influenza virus. Such VLPs, which contain HA from one subtype and NA from a different subtype, are formulated with a diluent or carrier as a bivalent immunogenic composition for immunizing vertebrates against infection caused by those two subtypes of influenza virus.

In yet another embodiment of this invention, it may be desirable to produce VLPs where a portion or all of the HA or NA is replaced by a heterologous moiety not produced by influenza virus, so as to comprise chimeric VLPs. Such moieties include, but are not limited to, a peptide, polypeptide or protein. Where only a portion of the HA or NA is to be replaced, a portion of the DNA sequence in the recombinant DNA molecule which encodes the HA or NA is replaced by a DNA sequence which encodes the non-influenza peptide, polypeptide or protein. Where the entire HA or NA is to be replaced, the entire DNA sequence in the recombinant DNA molecule which encodes the HA or NA is replaced by a DNA sequence which encodes the non-influenza peptide, polypeptide or protein.

In one aspects such non-influenza peptide, polypeptide or protein is from a pathogenic microorganism. These chimeric VLPs are formulated with a diluent or carrier as an immunogenic composition for immunizing vertebrates against infection caused by that pathogenic microorganism.

In another aspect, such non-influenza moiety is a pharmaceutically active moiety. These chimeric VLPs are formulated with a diluent or carrier as a pharmaceutical composition and administered in an amount effective for treating vertebrates with said such non-influenza moiety.

In still another aspect, the VLPs assemble and package RNPs, and may further incorporate and express a heterologous nucleotide sequence.

Any of the foregoing immunogenic and pharmaceutical compositions may further comprise an adjuvant.

BRIEF DESCRIPTION OF THE FIGURES

FIG. 2 depicts the structure of a VSV-G/HA chimera. The 14 amino acids of the cytoplasmic tail and 29 amino acids of the transmembrane domain of the influenza HA were fused in frame with the ectodomain of the VSV-G surface glycoprotein (SEQ ID NO:1).

FIG. 3 depicts western blot analyses of the influenza and VSV G proteins expressed in Sf9 cells infected by quadruple baculovirus recombinants (HA/Q28 or VSV-G/Q).

FIG. 8 depicts the analyses of VLP formation by Iodixanol gradient centrifugation.

FIG. 9 depicts western blot analyses of culture supernatants of Sf9 cells infected with M1 alone or HA/Q28 plus NP single baculovirus recombinants.

FIG. 11 depicts electron micrographs of immunogold labeled influenza VLPs.

FIG. 12 depicts western blots of influenza virus-infected cells probed with pools of sera from mice immunized with HA/Q28 VLPs.

FIG. 13 depicts blots of VSV-infected cells probed with pools of sera from mice immunized with VSV-G/Q chimeric VLPs. In FIG. 13A, results are depicted from pooled sera from a first pair of two mice. In FIG. 13B, results are depicted from pooled sera from a second pair of two mice. In each of FIGS. 13A and B: Lane 1: uninfected BHK cells as control; lane 2: VSV-infected BHK cells; lane 3: uninfected MDCK cells as control; lane 4: influenza-infected MDCK cells.

FIG. 14 depicts a quadruple baculovirus transfer vector carrying four genes of the influenza A/Udorn/72 (H3N2) strain, including the three genes encoding the polymerase subunits and the nucleoprotein. Transcription of the influenza genes PB1 and PA, which are positioned in opposite orientations, is driven by the polyhedrin promoter (abbreviated as "pH promoter"), whereas transcription of the PB2 and NP genes, also in opposite orientations, is driven by the p10 promoter. The four genes were subcloned into the baculovirus transfer vector PAcAB4, then co-transfected with linearized baculovirus DNA into Sf9 insect cells to generate the quadruple recombinant.

DETAILED DESCRIPTION OF THE INVENTION

The assembly and release of enveloped viral particles from the surface of virus-infected cells is a complex and stepwise process. It requires the concerted interactions of virus-encoded glycosylated and non-glycosylated proteins with discrete areas of the plasma membrane to initiate the assembly of the virion particle. In addition to these components, protein encapsidated nucleic acids, which represent the genetic material of the virus, are also incorporated into the structure to complete the morphogenesis process, which is completed by the pinching off or budding of the mature virion particle from the cell surface. The exact molecular interactions and the contributions of the different structural components in the assembly and final release of a complete virion particle are not well characterized.

The present invention describes the assembly and release of influenza virus-like particles (VLPs) from the surface of cells infected with recombinant vectors which expressed influenza virus structural proteins. A variety of expression systems is suitable for generation of VLPs. The invention is exemplified with insect cells infected with baculovirus recombinants which expressed influenza virus structural proteins.

In order to define the molecules required for influenza virus assembly and budding, a series of single gene and quadruple gene baculovirus recombinants was constructed. The recombinants expressed four influenza structural proteins (HA, NA, M1 and M2) in *Spodoptera frugiperda* 9 (Sf9) cells. Sf9 cells are an insect cell line (ATCC accession number CRL 1711) which is a derivative of the SF21 cell line. Although a transfer vector encoding all four structural proteins is described, the use of two to four transfer vectors which collectively encode these four proteins is also within the scope of this invention.

Figure 1:
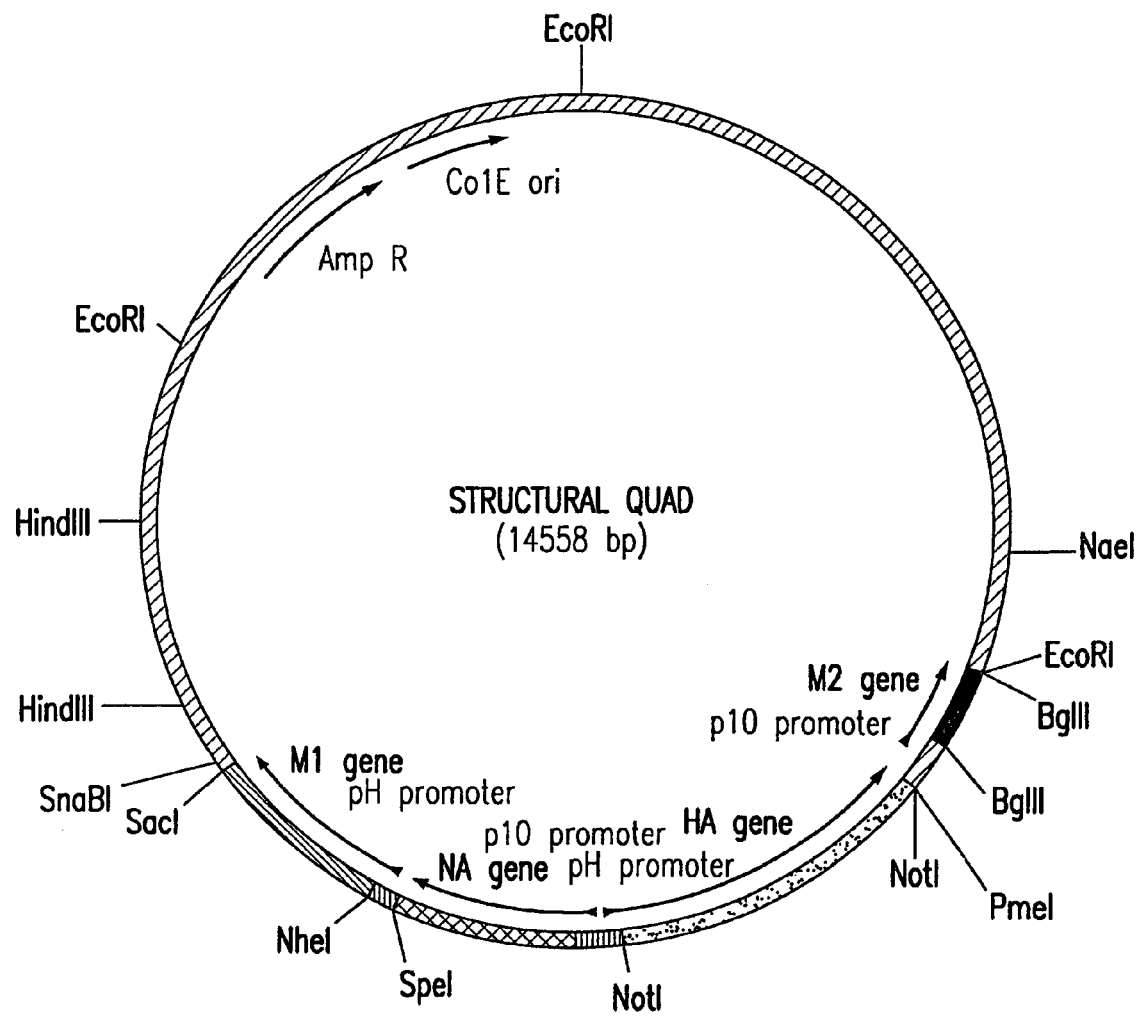
FIG. 1 depicts a quadruple baculovirus transfer vector (structural quad) carrying four genes of the influenza A/Udorn/72 (H3N2) strain. Transcription of the influenza genes HA and M1 are driven by the polyhedrin promoter (abbreviated as "pH"), whereas M2 and NA are driven by the p10 promoter. This vector was transfected together with linearized baculovirus DNA into Sf9 insect cells to generate the quadruple recombinant (HA/Q).

In order to obtain quadruple recombinants, a single baculovirus transfer vector encoding four structural proteins of the influenza A/Udorn/72 (H3N2) strain was constructed using a shuttle vector approach that facilitated cloning by reducing the size of the working plasmid and increasing the number of restriction sites. In the final transfer vector, the influenza genes were located downstream from the baculovirus promoters p10 (NA and M2) and polyhedrin (NA and M1), which were positioned to drive transcription of the genes in opposite directions (FIG. 1).

Quadruple (HA, NA, M1 and M2) baculovirus recombinants were obtained by simultaneous transfection of Sf9 cells with linearized viral DNA and transfer vector DNA. A few recombinant viral plaques were selected and further purified by two additional rounds of plaque to plaque isolation. Based on the level of protein expression assessed by immunoblot, this quadruple recombinant transfer vector, designated HA/Q28, was selected for use in subsequent experiments.

One prominent feature of this construct was that the donor and acceptor splicing sites on the M1 gene were mutated to prevent splicing of the M1 mRNA. Otherwise, M1 mRNA would have been spliced into M2 mRNA, resulting in a reduced level of expression of the M1 protein. The M2 DNA was introduced into the transfer vector as an independent gene.

In order to investigate whether the expression of these four influenza structural proteins was sufficient to drive assembly and budding of influenza VLPs from the surface of Sf9 insect cells infected with the quadruple baculovirus recombinant HA/Q28, culture supernatants were analyzed by western blot to ascertain the presence of M1 and HA proteins. Culture medium was harvested 72 hours post-infection, clarified at 4000×g for 30 minutes and the remaining suspended material then concentrated by centrifugation at 200000×g for two hours.

Figure 3A:
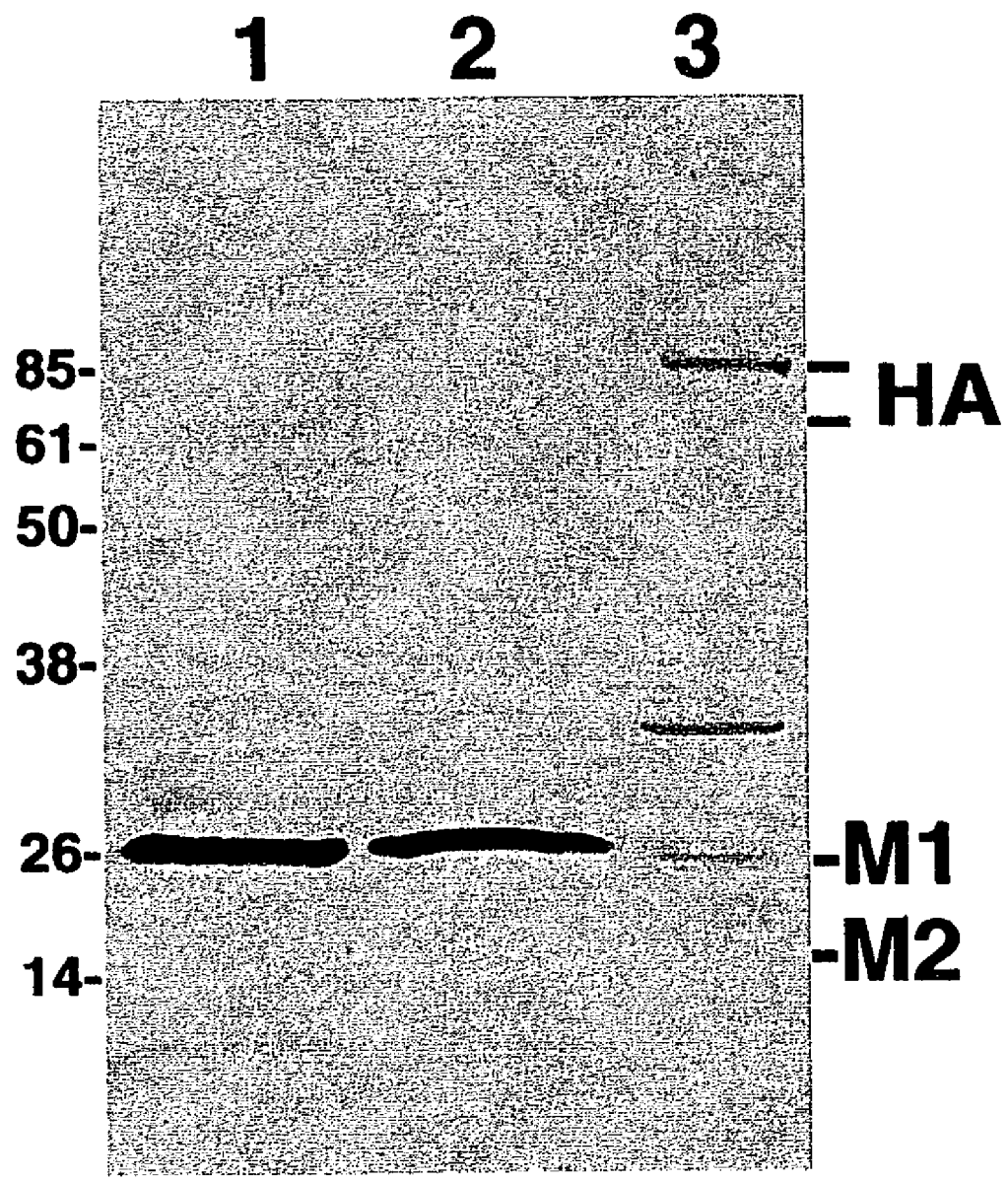
In FIG. 3A, the influenza proteins HA, M1 and M2 were detected in the supernatant of Sf9 cells infected with the quadruple recombinant HA/Q28 (72 hours post-infection), using a mixture of anti-HA, anti-M1 and M2 monoclonal antibodies (lane 1); the HA and M1 also were detected in the cell pellet (lane 2). Influenza A/Udorn/72 (H3N2)-infected MDCK cells were used as control (lane 3).

Western blot analysis of the concentrated supernatant from the infected cells probed with a combination of anti-HA, M1 and M2 monoclonal antibodies demonstrated significant expression of the influenza HA, M1, and M2 proteins (FIG. 3A). The HA protein appeared to migrate in different patterns than the HA from influenza A/Udorn/72 (H3N2)-infected Madin-Darby canine kidney (MDCK) cells, which may be a reflection of the various glycosylation forms of this protein. On the other hand, the migration patterns of the M1 and M2 proteins were similar to those expressed in MDCK influenza infected cells (FIG. 3A, lanes 1-3). The expression of the NA proteins was detected by western blot with a mouse polyclonal antibody that also recognized HA, M1 and M2 (data not shown).

The results discussed below demonstrate that the expression of four influenza structural proteins is sufficient for the assembly and budding of VLPs from the surface of Sf9 insect cells. Expression of nucleocapsid protein (NP), in addition to these four proteins, led to the formation of VLPs that incorporated the NP protein into the particle. Furthermore, the expression of M1 protein alone induced the release of VLPs, which can also incorporate the nucleocapsid NP when co-expressed with M1. In addition, replacing the HA gene by either a full length G-protein of Vesicular stomatitis virus or a hybrid HA/G in the quadruple recombinant, induced the assembly and release of chimeric VLPs. All of these VLPs are obtained by conventional means of purification after the secretion of the VLPs into the medium.

In order to evaluate whether heterologous, non-influenza glycoproteins can be incorporated into the surface of the influenza VLPs, two different chimeric quadruple baculovirus recombinants were constructed. The first, designated VsV-G/Q, replaced the DNA sequence encoding the influenza HA protein with a DNA sequence encoding the full-length glycoprotein G of Vesicular stomatitis virus (VSV). The second, designated VSV-G/HA-Q, carried a hybrid DNA sequence encoding the ectodomain of the VSV G protein and the transmembrane domain and cytoplasmic tail of the influenza HA protein (see FIG. 2). Both recombinants contained the genes for the three structural influenza virus proteins M1, NA and M2.

These constructs were subjected to the same characterization studies as the wild-type influenza VLPs and the results indicated that infection of Sf9 insect cells with either construct directed the assembly and release of influenza-like particles bearing the VSV G proteins on their surface. Both of these recombinant viruses were able to drive the expression of the four proteins (M1, M2, NA and VSV-G), which were also secreted into the medium.

Figure 3B:
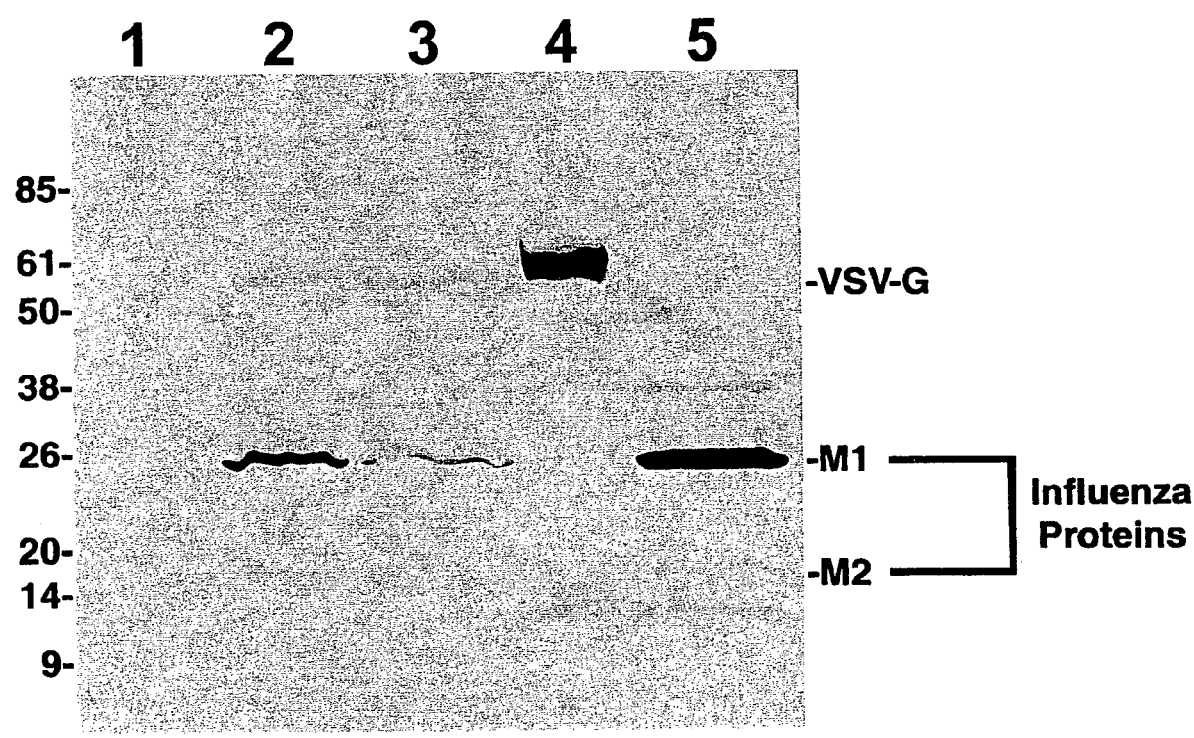
FIG. 3B depicts the expression of the VSV G, as well as influenza M1 and M2 proteins, in Sf9 cells infected with VSV-G/Q (full length G). Expression was detected in cell pellets (lane 2) and culture supernatant (lane 3), when probed with a mixture of anti-G, anti-M1 and M2 monoclonal antibodies. Uninfected Sf9 cells (lane 1), VSV-infected BHK cells (lane 4) and influenza A/Udorn/72 (H3N2)-infected MDCK cells (lane 5) were used as negative and positive controls respectively.

Western blot analysis of Sf9 cells infected with VSV-G/Q showed that the VSV G protein, as well as influenza proteins M1 and M2, were expressed 72 hours post-infection (FIG. 3B). Furthermore, concentrated supernatant of infected cells showed a positive western blot when probed with antibodies to VSV G, and influenza M1 and M2 (FIG. 3B, lane 3).

The methods just described for the VSV G protein are readily applicable to the incorporation of other non-influenza glycoproteins of biological interest into the surface of the VLPs, as well as the incorporation of a moiety not produced by influenza virus. Such moieties include, but are not limited to, a peptide, polypeptide or protein. As discussed below, such VLPs are used as immunogenic compositions, in receptor-ligand interaction studies, and/or as a system for the delivery of the non-influenza moiety as part of a pharmaceutical composition.

Figure 4A:
FIG. 4 depicts the immunofluorescence analysis of Sf9 cells infected with a quadruple baculovirus recombinant (HA/Q28). Box cultures of Sf9 cells were infected with HA/Q28 at an MOI of 1 and incubated for 72 hours. At that time, individual boxes were fixed with methanol-acetone and incubated sequentially with primary and secondary antibodies. Expression of HA (FIG. 4A), M1 (FIG. 4B) or HA/M1 (FIG. 4C) was detected using the appropriate filters.
Figure 4B:
Figure 5A:
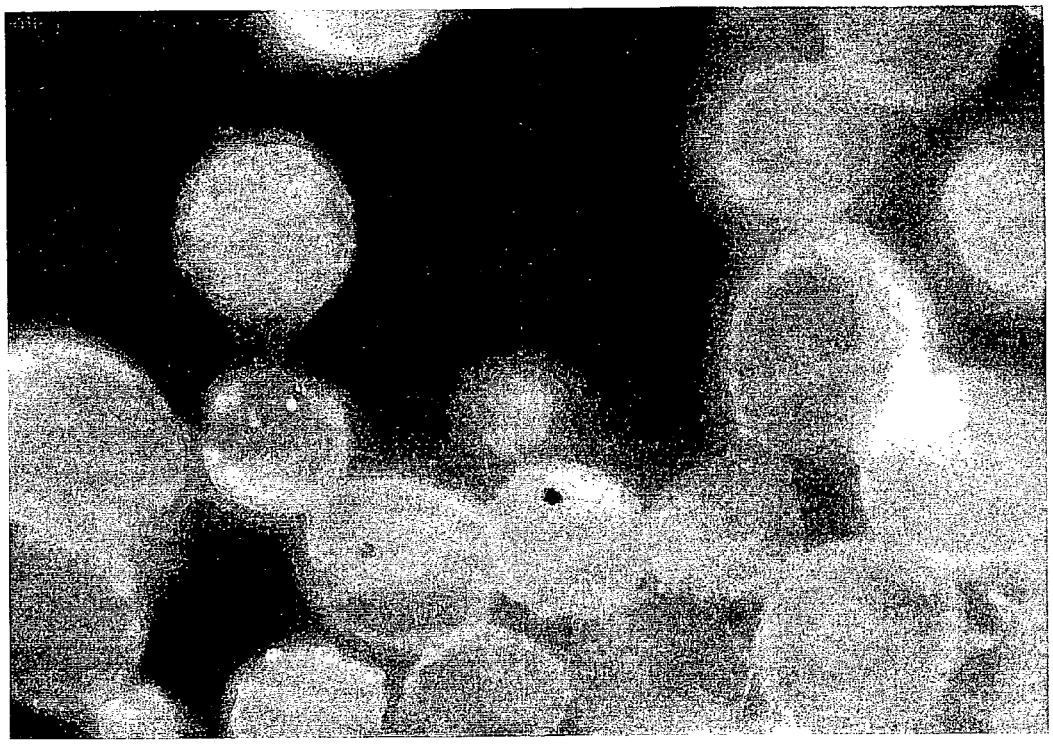
FIG. 5 depicts the immunofluorescence analysis of Sf9 cells infected with HA/Q28. Box cultures were infected with HA/Q28 at an MOI of 1 and incubated for 72 hours. At that time, individual boxes were fixed with paraformaldehyde and incubated sequentially with primary and secondary antibodies. Expression of HA (FIG. 5A), NA (FIG. 5B) or HA/NA (FIG. 5C) was detected using the appropriate filters.
Figure 5B:
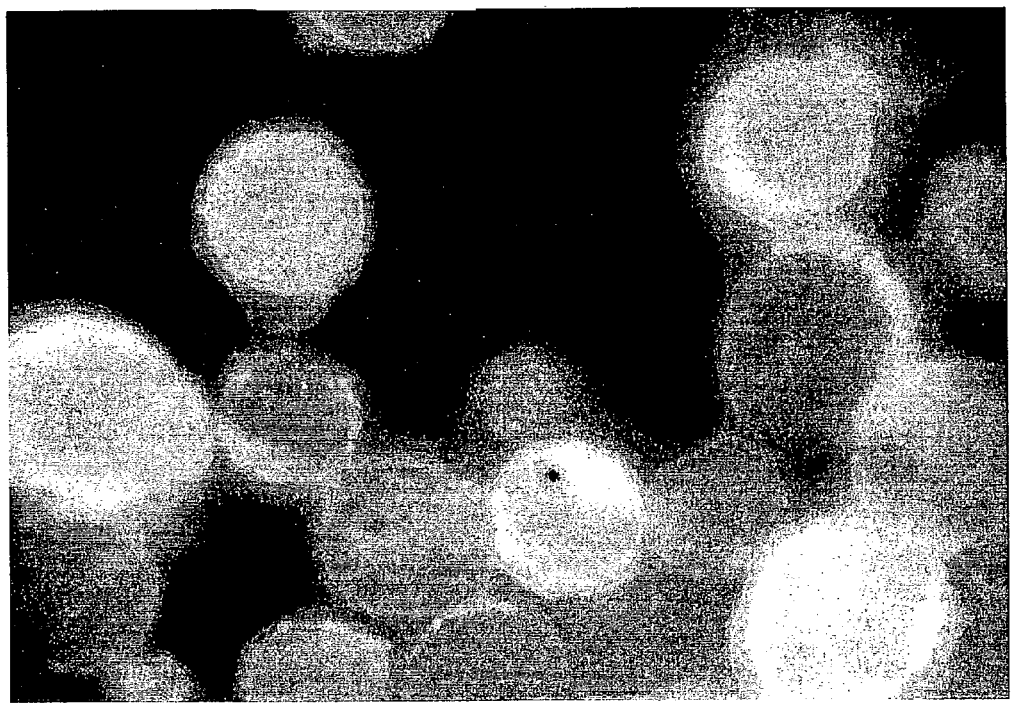
Figure 5C:
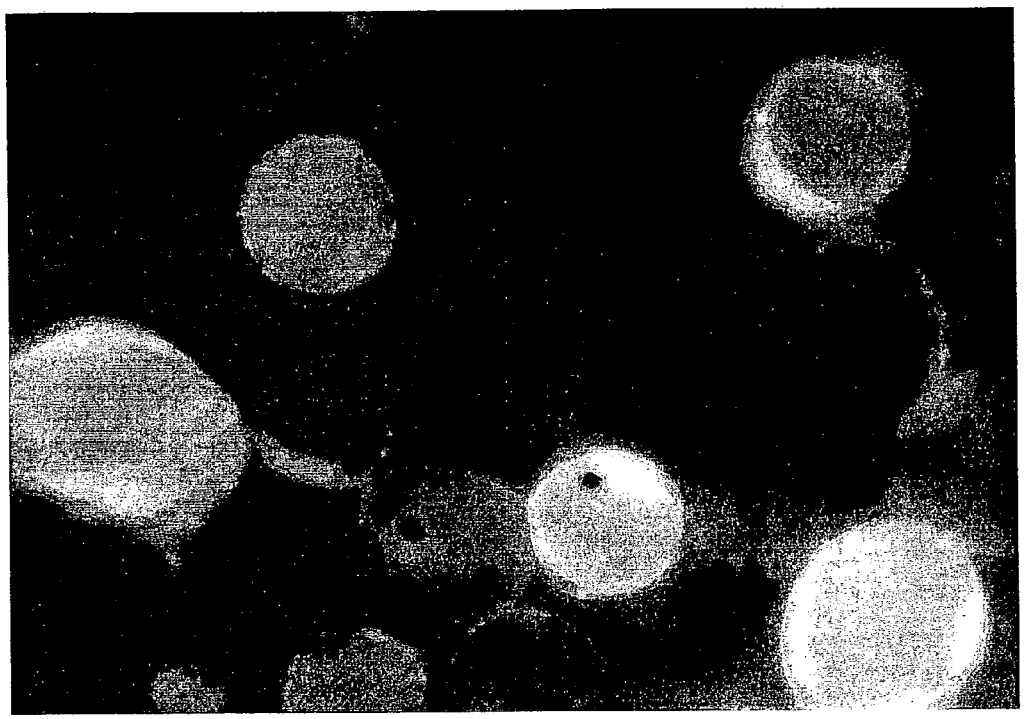
Figure 6:
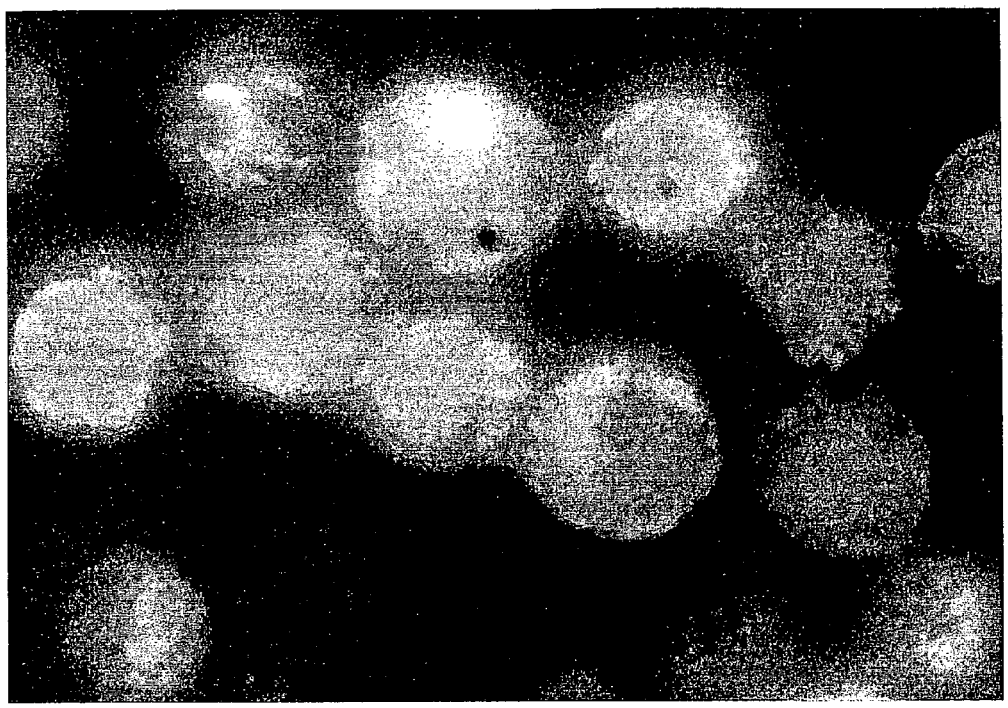
FIG. 6 depicts the immunofluorescence analysis of Sf9 cells infected with HA/Q28. Box cultures of Sf9 cells were infected with HA/Q28 at an MOI of 1 and incubated for 72 hours. At that time, individual boxes were fixed with paraformaldehyde and incubated sequentially with primary and secondary antibodies. Expression of M2 was detected using the appropriate filters.
Figure 7:
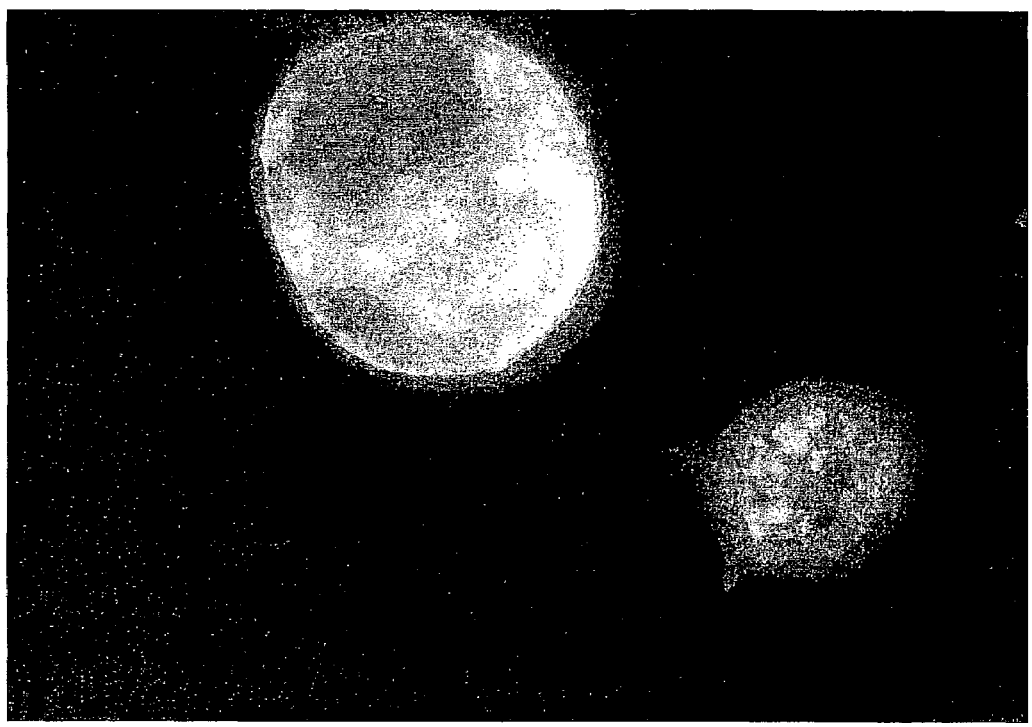
FIG. 7 depicts the immunofluorescence analysis of Sf9 cells infected with VSV-G/Q (full length influenza HA gene in HA/Q28 replaced by full length VSV G gene). Box cultures were infected with VSV-G/Q at an MOI of 1 and incubated for 72 hours. At that time, individual boxes were fixed with methanol-acetone and incubated sequentially with primary and secondary antibodies. Expression of VSV G was detected using the appropriate filters.

To further evaluate expression and cellular localization of the influenza proteins in Sf9 cells, immunofluorescent analysis of cells infected with the plaque purified baculovirus recombinant HA/Q28 was conducted. These experiments showed that the four influenza structural proteins were expressed as shown by indirect immunofluorescence (FIGS. 4-6). Dual-staining experiments with anti-HA and anti-NA antibodies demonstrated that these surface glycoproteins localized at the periphery of the infected cells with a certain degree of overlap (FIG. 5C). These results suggested that these major glycoproteins co-localized at discrete areas on the surface of the infected insect cells, which resembles what is expected in a natural influenza infection of mammalian cells.

Figure 4C:
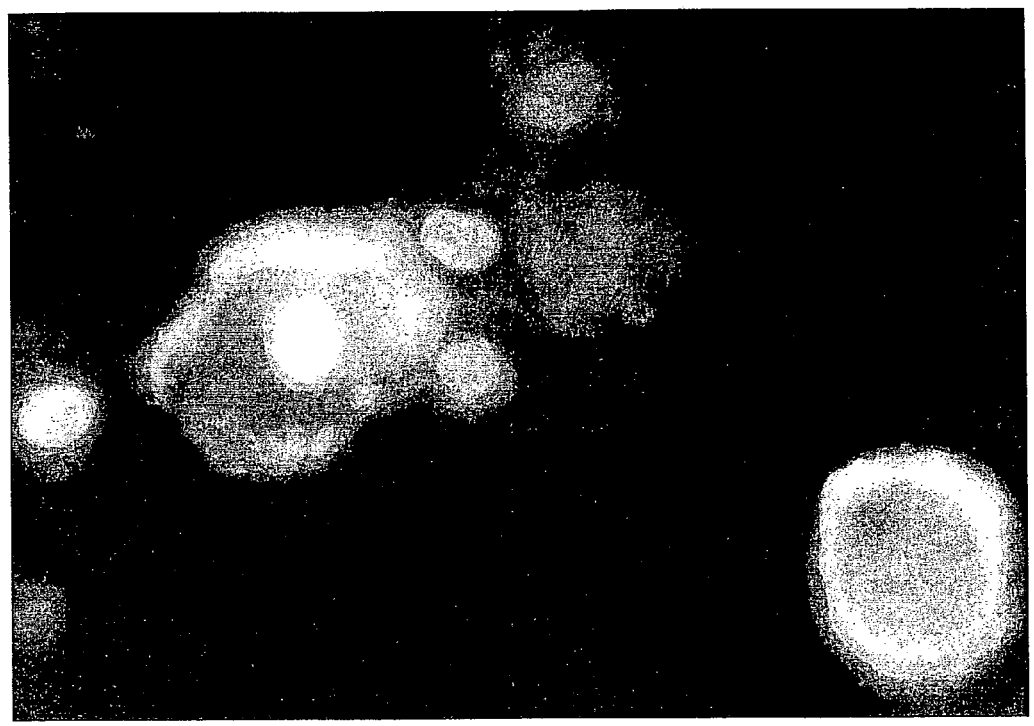

Similarly, double immunofluorescent staining of HA/Q28-infected Sf9 cells with a mixture of monoclonal antibodies to either HA and M1 showed that the surface proteins and matrix M1 seemed to co-localize in distinct areas of the cell membrane (FIG. 4C).

On the other hand, immunofluorescence of M1-baculovirus recombinant infected Sf9 cells showed that M1 protein predominantly accumulated in the nuclei of the infected cells and only minor amounts were visualized at the cell surface (data not shown). The distribution pattern of M1 protein in infected cells did not appear to be altered whether M1 was expressed as a single gene or as a quadruple recombinant together with HA, NA and M2 (FIG. 4). In addition, simultaneous infection of Sf9 cells with M1 and NP single recombinants did not show redistribution of these proteins in the cells as compared to Sf9 cells infected individually with either M1 or NP recombinants (data not shown).

Thus, western blot and immunofluorescent analysis of infected cells clearly showed that these four proteins not only were present in the cells and cell supernatants, but also co-localized at discrete areas on the plasma membrane. This suggested a potential association between these structural proteins.

Immunofluorescence studies of Sf9 cells infected with a VSV-G/Q recombinant showed that the VSV G protein is not only expressed, but also appears to accumulate in the periphery of the infected cells.

Because immunofluorescent studies revealed that these proteins co-localized at the cell surface, this led to an evaluation of whether these four viral proteins were sufficient to drive the formation and release of VLPs from the surface of the infected cell. Specifically, in order to investigate whether these proteins were released from the cell as a consequence of cellular damage and death, or because they assembled as VLPs that budded from the cell surface, concentrated supernatants from HA/Q28-infected Sf9 cells were subjected to Iodixanol (26) velocity gradient centrifugation (200000×g for 3.5 hours). As individually specified, fractions containing the proteins of interest were subjected to additional purification on a 20-60% sucrose gradient.

Figure 8A:
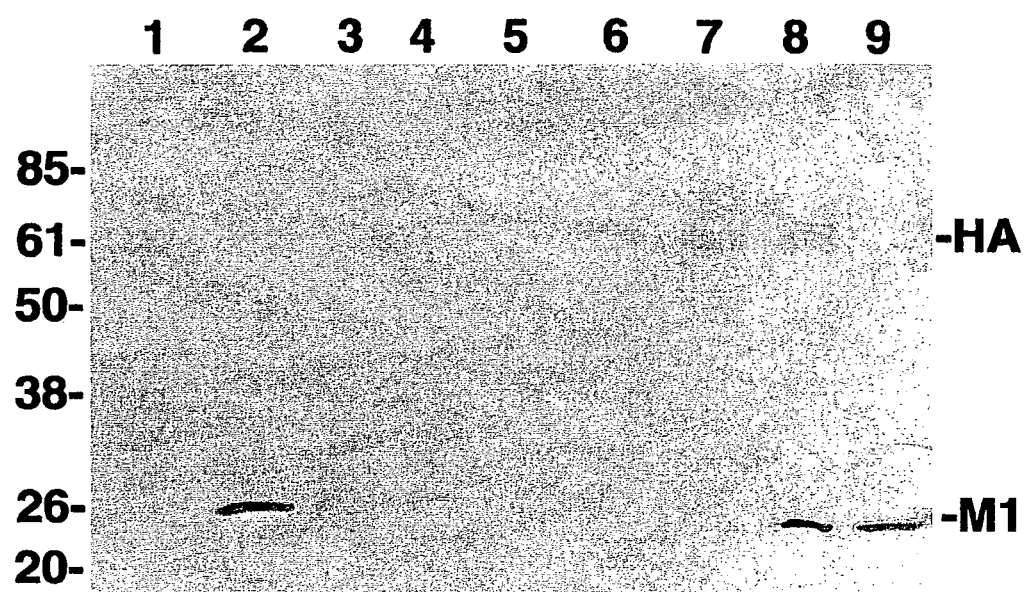
FIG. 8A depicts the results when fractions from HA/Q28 were probed by western blot with a mixture of anti-HA and M1 monoclonal antibodies. Lanes 1-8 represent fractions collected from top to bottom of the tube; lane 9 is a MDCK influenza A/Udorn/72 (H3N2)-infected control.

Western blot analysis of collected fractions showed that HA and M1 co-migrated through the gradient, reaching a peak concentration in fraction 2 (FIG. 8A, lane 2). These proteins were also found in adjacent fractions 3 and 4, as well as in fractions 7 and 8 (FIG. 8A). Detection of HA and M1 in these lower fractions (toward the bottom of the gradient) was likely due to the association of these proteins with the baculovirus, which under these conditions bands in fractions 7 and 8 (data not shown).

Figure 8B:
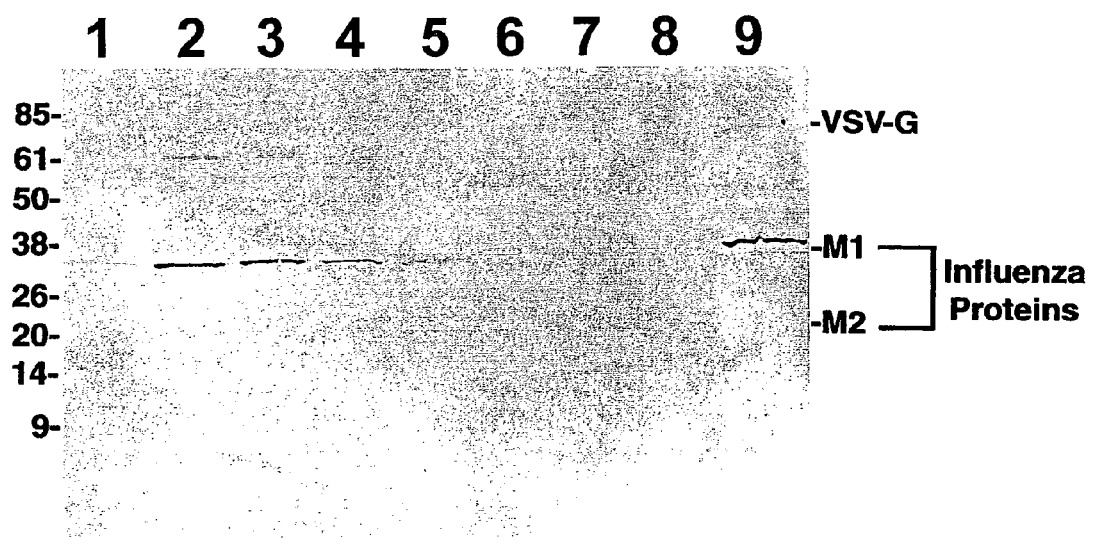
FIG. 8B depicts the results when fractions from VSV-G/Q were probed by western blot with a mixture of anti-VSV-G, anti-M1 and anti-M2 monoclonal antibodies. Lanes 1-8 represent fractions collected from the top to the bottom of the tube; lane 9 is a mixture of VSV-infected BHK and influenza-infected MDCK cells combined as a control.

A similar experiment was conducted with the VSV-G/HA-Q (chimera) and VSV-G/Q (full length) constructs. As was observed with the HA/Q28, fraction 2 of an Iodixanol gradient contained the VSV G and the influenza M1 and M2 proteins as shown by western blot analysis (FIG. 8B, lane 2). When Sf9 cells were infected with a quad recombinant carrying a full length VSV-G instead of HA, all the probed proteins (VSV-G, M1 and M2) were also present in both concentrated supernatant and fractions 2 and 3 of the Iodixanol gradient (FIG. 3B, lane 3 and FIG. 8B). These results suggested that infection of Sf9 cells with either quad VSV-G/HA-Q (chimera) or VSV-G/Q (full length) directed the assembly and release of influenza VLPs bearing the VSV G protein on their surface.

Figure 9A:
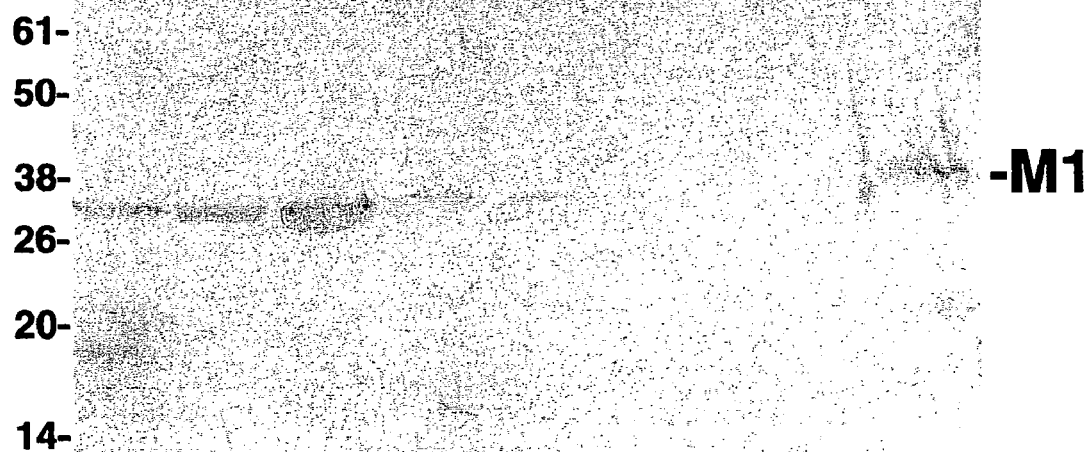
FIG. 9A depicts the analysis of fractions derived from the supernatant of single M1 infection, which were probed with anti-M1 antibody. Lanes 1-8 represent fractions collected from the top to the button of the tube; lane 9 is influenza-infected MDCK cells as control.

In view of the fact that some of the HA/Q28 particles examined under the electron microscopy did not show detectable surface spikes (see below), the question arose of whether the influenza matrix protein by itself is sufficient to drive assembly and release of vesicular particles. To address this question, Sf9 insect cells were infected with an M1 baculovirus recombinant for 72 hours, and concentrated culture supernatants were subjected to the same analysis as described above. Immunoblot analysis of Iodixanol gradient supernatant fractions demonstrated that matrix protein was concentrated in fractions 2 and 3, similar to the migration pattern of the VLPs released from Sf9 cells infected with HA/Q28 (FIG. 9A).

Figure 9B:
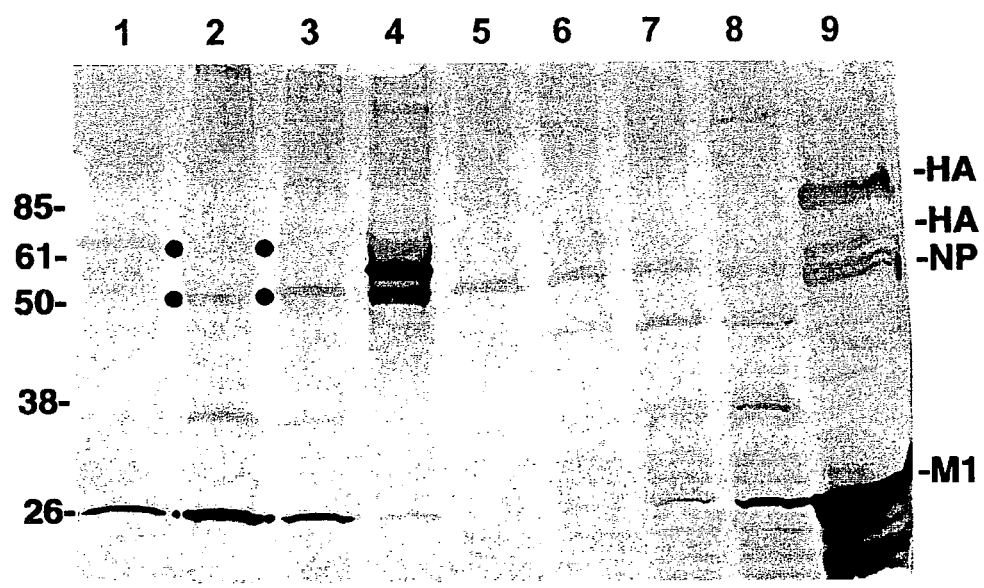
FIG. 9B depicts the results when supernatant of dually-infected Sf9 cells (HA/Q28 plus NP single baculovirus recombinants) were purified and probed with a mixture of anti-HA, anti-M1 and anti-NP antibodies. Lanes 1-8 represent fractions collected from the top to the bottom of the tube; lane 9 is the sane control as in FIG. 9A.

There is strong evidence (3) that the matrix protein (M1) plays an important role in the transport of the ribonucleoprotein complex (RNPs) from the nucleus to the cell surface, where viral assembly takes place. Association between the matrix and RNPs could be mediated through contacts with NP, virion RNA or both. Therefore, it was of interest to evaluate whether the nucleocapsid protein (NP) was incorporated into the VLP when Sf9 cells were co-infected with the quadruple recombinant HA/Q28 and an NP single baculovirus recombinant. Western blot analysis of gradient fraction 2 demonstrated that the nucleocapsid protein NP was indeed incorporated into the resulting VLPs (FIG. 9B). This result raised the question as to which proteins establish contact with NP in order to allow the incorporation of NP into the particle.

Figure 8C:
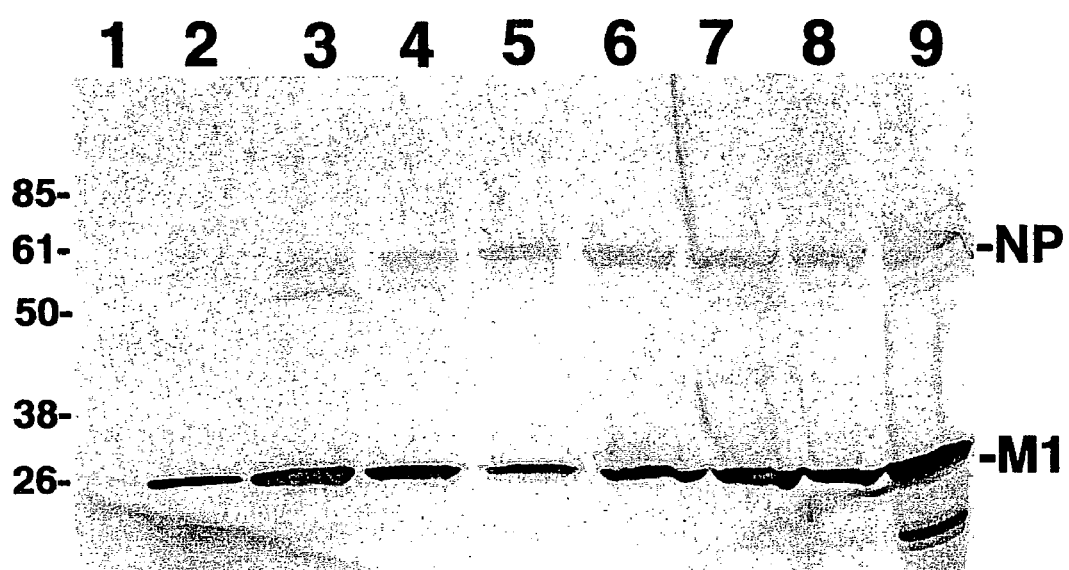
FIG. 8C depicts the results when concentrated supernatants of dually infected (M1 and NP single recombinant) Sf9 cells were purified and probed with a mixture of anti-M1 and anti-NP antibodies. Lanes 1-8 represent gradient fractions collected from the top to the bottom of the tube; lane 9 is influenza-infected MDCK cells as control.

To address this question, M1 and NP single baculovirus recombinants were used. Simultaneous expression of M1 and NP in Sf9 cells produced membrane particles composed of both proteins. This allowed the evaluation of potential interactions between these two proteins in the absence of defined influenza RNA with precise termini. Western blot analysis of gradient purified particles derived from Sf9 cells doubly infected with M1 and NP recombinants showed that M1 and NP co-localized in the same fractions (FIG. 8C). On the other hand, infection with an NP recombinant alone did not induce particle release and did not demonstrate the presence of reactive NP in any of the fractions (data not shown). These results suggested an interaction between M1 and NP which was strong enough to bring NP into the M1-containing particle even in the absence of RNA.

Based on the localization of NP protein in the influenza virus, and other studies of protein particle assembly (10), it is reasonable to infer that the NP protein establishes contact with the matrix protein M1 and, as a result of this interaction, gets incorporated into the VLP. In influenza-infected cells, transport of RNPs from the nucleus to the site of virus assembly at the plasma membrane occurs after association with the matrix protein by a mechanism not well characterized.

It has been shown (27) that NP protein binds not only to influenza RNA, but may also bind with lower affinity to nonspecific RNA. Therefore, this result does not rule out the possibility that RNA is required for a productive interaction between M1 and NP.

Therefore, it is concluded that the matrix protein not only initiates molecular interactions leading to assembly and release of particles, but also is able to bind and incorporate the nucleocapsid NP into the particle. In influenza infected cells, the MI protein associates with the RNPs in the process of transport and viral assembly. In the case of single M1 recombinants, these other influenza structures are not present, yet budding still occurs. NP may associate with M1 as monomers or oligomers, or after binding cellular RNA. Whatever is the nature of the association, it is clear that M1 and NP expressed in insect cells bind with sufficient affinity to assemble into a vesicle, which is able to exit from the cell.

To characterize further the nature of the association among the influenza proteins that co-migrated into fractions 2 and 3, electron microscopy evaluation of the material present in these fractions was carried out.

Figure 10:
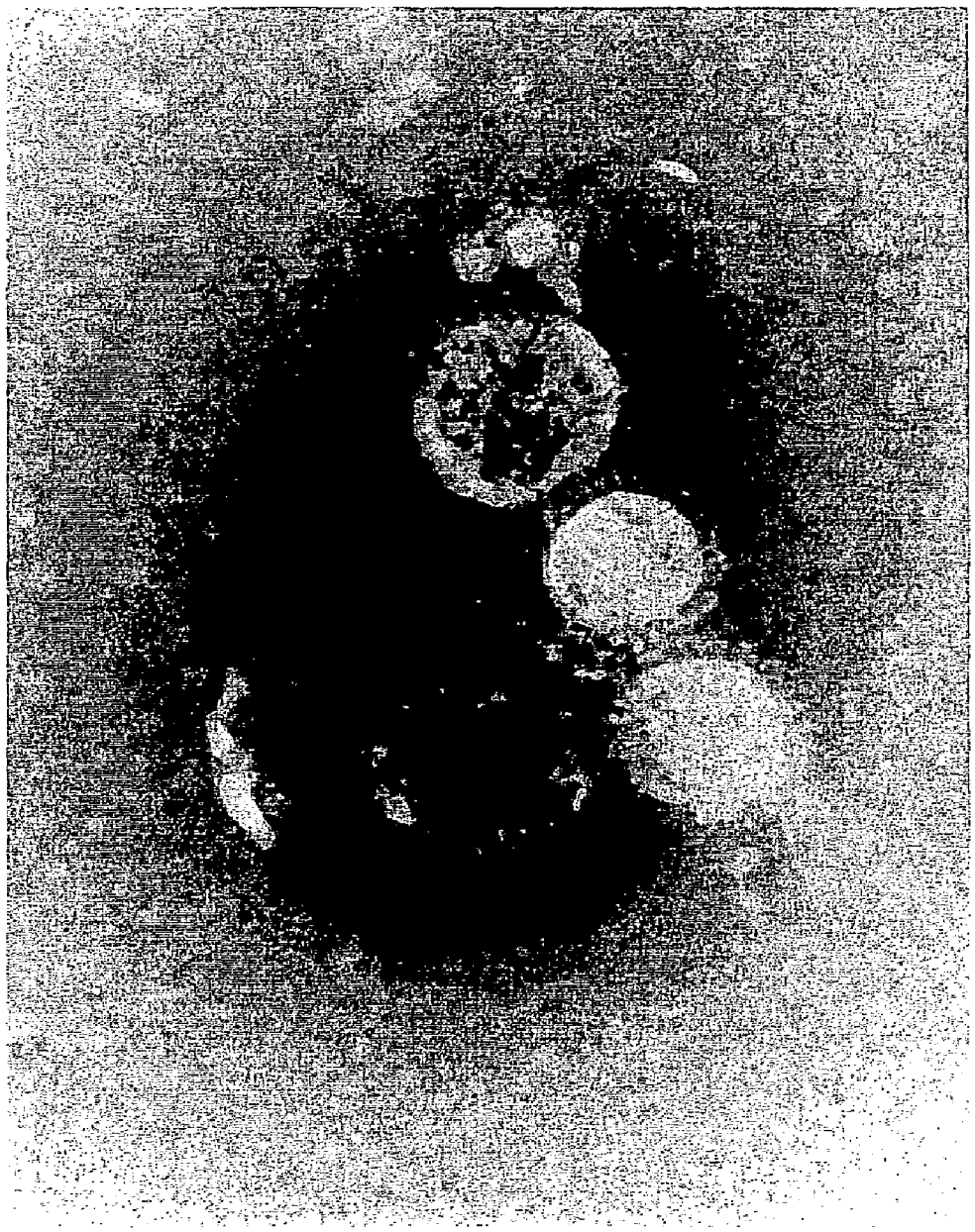
FIG. 10 depicts an electron micrograph of negatively stained influenza VLPs purified from culture media of sf9 cells infected with a quadruple recombinant HA/Q28.

Electron microscopic examination of fraction 2 revealed the presence of a high concentration of both vesicular and non-vesicular particles studded with surface projections that greatly resembled influenza virus and subviral particles (FIG. 10). The shape and structural features of the VLPs varied depending on their positions in the gradient. The spikes protruding from the surface of some vesicles appeared similar to influenza HA and NA, in that they thrust outward from the surface of the particles as they do from the surface of influenza virus.

The projections in some VLPs from fraction 2 were significantly similar to the HA spikes present in influenza virus (FIG. 10). The morphology of NA is less distinctive in samples containing such a wide range of spike-studded entities. Fraction 3 contained a similar range of particles in high concentration, however it appeared to contain a higher concentration of aggregated membranes than fraction 2 (data not shown).

Fractions that showed the largest number of influenza VLPs under the electron microscope also contained the highest concentrations of M1 and HA proteins as demonstrated by western blot analysis. The VLPs, which were covered with surface projections and ranged in length from about 75 nm to 150 nm, clearly resembled influenza virus in size and morphology.

To characterize further the structure of the M1 particles, these two fractions of the gradient were examined by electron microscopy. Negative stained electron microscopy examination showed a large number of vesicles of variable shapes that did not bear spikes on their surfaces (data not shown).

In order to determine whether baculovirus-infected cells spontaneously released vesicles or whether association of M1 protein at the cell surface was sufficient to drive the particle exit, similar gradient fractions of concentrated supernatants of Sf9 cells infected with either wild-type or NP recombinant baculovirus were examined by electron microscopy. None of the other proteins (NP, HA) were detected in these fractions, when the supernatant of Sf9 cells infected with the corresponding single recombinants were used in the analysis. These results indicated that the matrix protein by itself was sufficient to drive assembly and release of VLPs from the surface of insect cells.

Figure 11A:
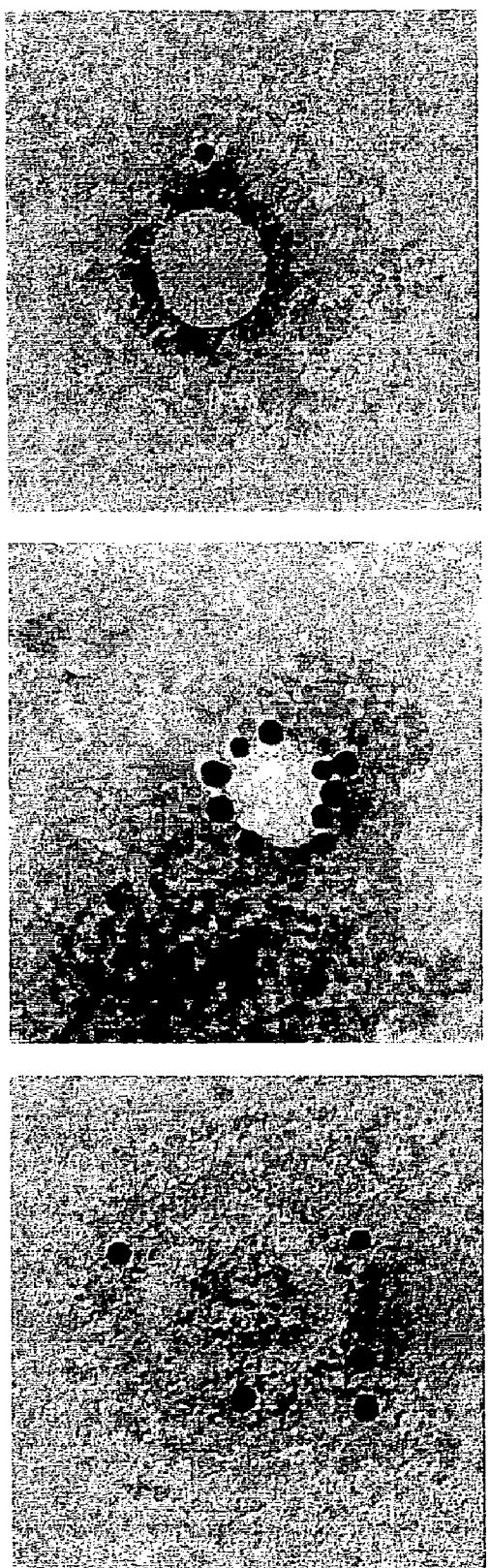
In FIG. 11A (three views), VLPs were probed with an anti-HA monoclonal antibody and counterstained with gold spheres coupled to anti-mouse IgG.
Figure 11B:
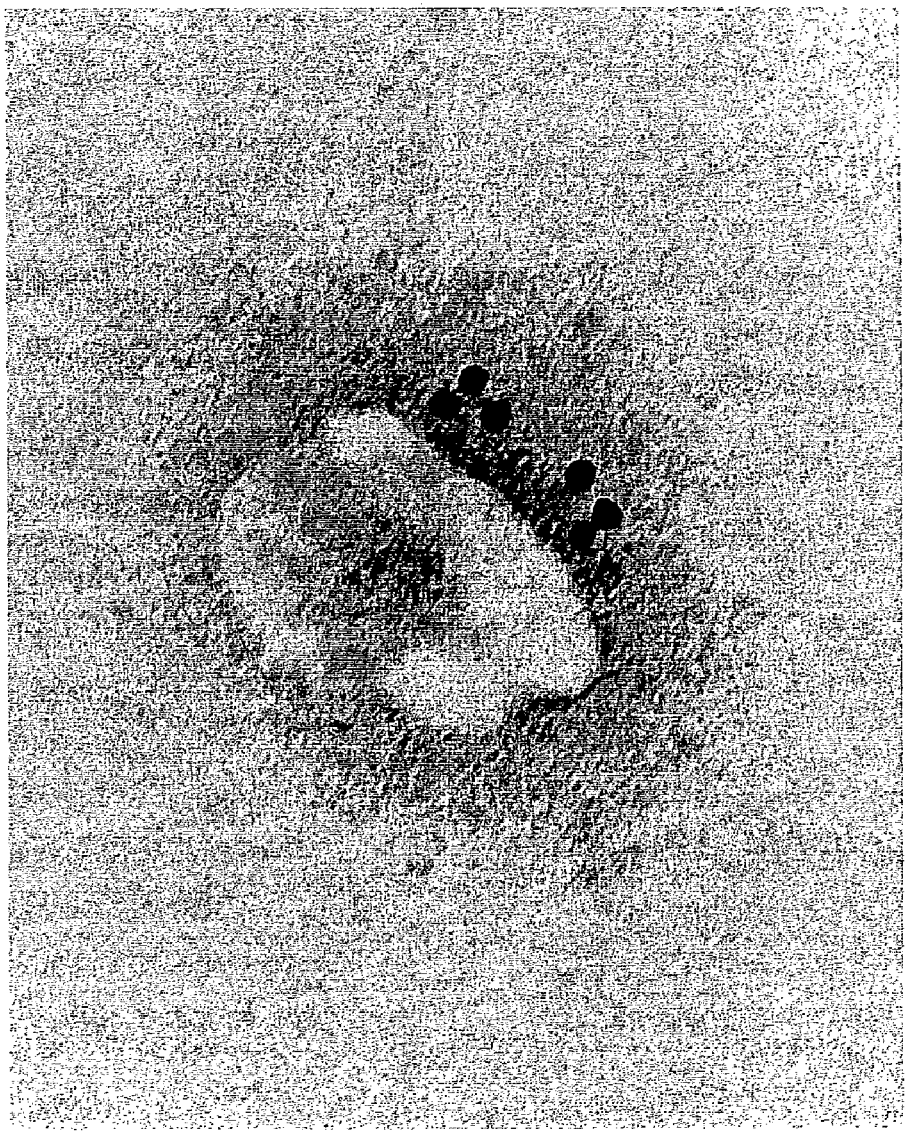
In FIG. 11B, VLPs were probed with anti-NA monoclonal antibody and counterstained as in FIG. 11A.

The protein composition of the spikes protruding from the surface of the VLPs was investigated by electron microscopy of immunogold labeled surface antigens that were probed with specific monoclonal antibodies to the HA, and NA (which were the same as those used in immunofluorescence experiments). This examination showed that the major influenza surface antigen HA was indeed present on the surface of the VLPs, as indicated by the presence of gold beads (FIG. 11A). This confirmed what was assumed from the structural evaluation of the spikes visualized by negative staining and electron microscopy (FIG. 10). Similarly, immunogold labeling with anti-NA antibody and electron microscopy also revealed the presence of NA glycoprotein on the surface of the VLPs, although with lower abundance than HA (FIG. 11B).

Attempts were made to detect the presence of the M2 proteins on the surface of the VLP by immunogold labeling using a rabbit polyclonal antibody raised against peptides encompassing 18 amino acids of the amino-terminal of M2 protein. M2 protein was not detected on the surface of the particle, even though it was present in the gradient fractions subjected to immunogold labeling-electron microscopy (IEM). However, this was not surprising, because IEM is not a sensitive enough system to detect minor proteins and, even with native influenza virus, very little M2 is produced and is difficult to detect.

When the chimeric influenza-VSV VLPs were purified and examined by electron microscopy, they were found to have a morphology similar to the influenza VLPs. In addition, immunogold labeling analysis revealed that they bore surface glycoproteins that were reactive with anti-G antibody (data not shown).

Particles generated with either construct did not appear to show any significant difference in morphology. The content of G proteins on the surface of both particles was apparently similar. This suggested that the potentially favorable interaction between the HA portion of the G/HA chimera and the M1 underlying the membrane did not enhance significantly the level of incorporation of G into the particle.

To evaluate the immunogenicity of the wild-type influenza VLPs and chimeric VLPs (containing VSV G), two groups of Balb/c mice were immunized via the intramuscular route with either HA/Q28 or VSV-G/Q, where each set of VLPs was formulated with aluminum phosphate. All mice in each group received a prime and two booster injections at two-week intervals. Two weeks after the last immunization, blood samples were obtained and the presence of antibodies against the corresponding antigen were evaluated by western blot (for both types of VLPs), inhibition of hemagglutination (for the HA/Q28) and a serum-neutralization test (for VSV-G/Q).

Figure 12A:
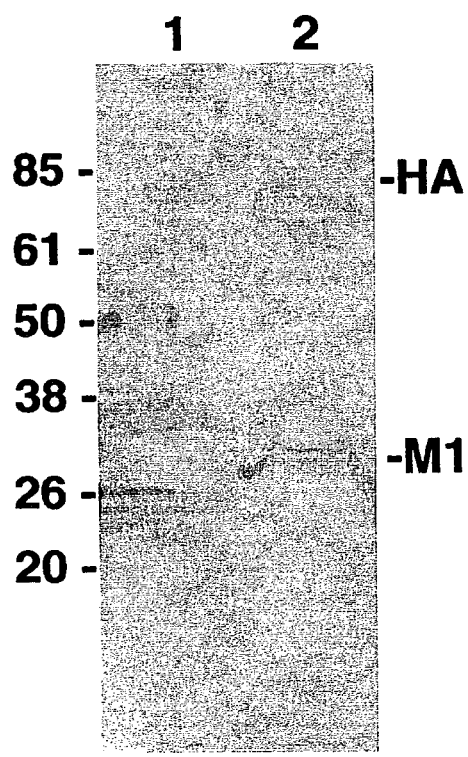
In FIG. 12A, results are depicted from pooled sera from a first pair of two mice.

Immunoblot analysis demonstrated that the sera from mice immunized with the influenza BA/Q 28 recognized the influenza virus used as the test immunogen (predominantly HA and M1; FIGS. 12A and B, lane 2). Similarly, sera from mice immunized with the chimeric VLPs VSV-G/Q recognized the G protein of VSV (FIG. 13A and B, lane 2).

Performance of an inhibition of influenza virus hemagglutination test (IHA) showed that sera from HA/Q28 immunized mice had an IHA titer of 96 IHAU, which was more than two-fold higher than that obtained from control naive mice (32 IHAU). This response was almost equal to the IHA titer of 128 IHAU elicited by two intranasal immunizations (two weeks apart) with live influenza A/Hong Kong (H3N2) (courtesy of by Dr. Mbawuike, Baylor College of Medicine), which served as a positive control.

Neutralization of VSV by sera from mice immunized with VSV-G/Q showed that a dilution as high as 1/64 completely neutralized a standard titer of VSV, thereby preventing the formation of any plaques in the cell monolayer.

These results demonstrated that the influenza VLPs elicited an antibody response that not only recognized wild-type influenza virus in western blot, but also inhibited influenza virus hemagglutination. Moreover, immunization of mice with chimeric VLPs carrying the VSV G protein induced a humoral antibody response that recognized the VSV G protein of wild-type virus in a western blot, and also prevented VSV infection in a serum neutralization test.

Other types of host cells besides insect cells may also be used with one or more recombinant vectors encoding infuenza virus structural proteins (and, if desired, a non-influenza protein) in order to produce VLPs. Studies with the M protein of VSV demonstrated that this property was shown in both insect (8) and mammalian (7) cell types. In addition, expression of matrix M and NP proteins of parainfluenza virus (another non-segmented, negative-stranded RNA virus) in mammalian cells led to the formation and release of virus-like particles (10).

Other cell types suitable for use as host cells include mammalian (such as Chinese hamster ovary, chick embryo fibroblasts, BHK cells, human SW13 cells) and yeast (such as *Pichia, Saccharomyces*) host cells. The use of mammalian or yeast cells may result in the expression of proteins with glycosylation more like that of wild-type proteins than can be obtained with insect cells.

Suitable recombinant vectors for delivery of genes in addition to baculovirus include, but are not limited to, viruses such as vaccinia and other poxviruses, sindbis, adenoviruses, Venezuelan equine encephalitis virus and other alphaviruses, as well as plasmid DNA.

The recombinant vectors should include promoters and other regulatory elements (such as a polyadenylation signal) effective to direct the expression of influenza (and any non-influenza) proteins to produce VLPs in the corresponding host cell type. Host cells are transfected, infected or otherwise transformed by conventional techniques known in the art. Such techniques also include, but are not limited to, transduction, electroporation and lipofection.

As described herein, the expression via a quadruple baculovirus recombinant of the four structural proteins of influenza (HA, NA, M1, M2) was sufficient to drive the assembly and release of VLPs from the surface of Sf9 insect cells. This is the first report of the formation of influenza VLPs produced with only four structural proteins. Indeed, VLPs can comprise as few as one structural protein, M1. Therefore, this invention includes VLPs composed of M1 alone, M1 plus one or two of HA, NA and M2, as well as all four of these structural proteins.

The assembled VLPs closely resemble the wild-type influenza virus in their size, particle morphology and fine structure of the surface spikes. Furthermore, formation of VLPs in the absence of influenza RNPs indicates that RNPs are not necessary for the assembly and release of particles.

This novel approach to assemble influenza VLPs is of great importance for the design of immunogenic compositions against new influenza variants. One important feature of this system is the ability to replace the surface glycoproteins with different subtypes of HA and/or NA; this will permit the updating of formulations with new antigenic variants of these proteins. As antigenic variants of these glycoproteins are identified, the VLPs can be updated to include these new variants. Thus, even extremely dangerous surface glycoproteins such as H1N1 (from the 1918 Spanish flu) or an HA, NA combination with pandemic potential could be incorporated into VLPs without concern about the implications of releasing genes that had not circulated in humans for several decades. This is because the VLPs are not infectious, do not replicate and cannot cause disease.

Furthermore, the feasibility of incorporating heterologous glycoproteins onto the surface of the VLPs makes this approach attractive not only as a delivery system, but may also allow for the targeting of specific cell types (tropism) based upon the surface glyocoproteins incorporated onto their surfaces. In one embodiment, the VLPs contain the cytoplasmic tail and transmembrane domain of HA and the external domain of a non-influenza glycoprotein, which facilitates the generation of chimeric particles useful for multivalent immunizations.

In summary, it has been shown that wild-type and chimeric influenza virus-like particles can be assembled and released from the surface of Sf9 cells following expression of only one to four viral structural proteins, as long as the matrix protein M1 is always expressed. It has also been demonstrated that M1 is able to drive the release of vesicular particles that contain NP when the two are present together.

In a further embodiment of the invention, the formation and subsequent encapsidation of ribonucleoprotein complexes (RNPs) (containing the three polymerase subunits, PA, PB1 and PB2, as well as the nucleoprotein, NP) into the VLPs was achieved. A second quadruple baculovirus recombinant was generated (FIG. 14) that simultaneously expressed in Sf9 insect cells the three polymerase subunits and NP.

Figure 15:
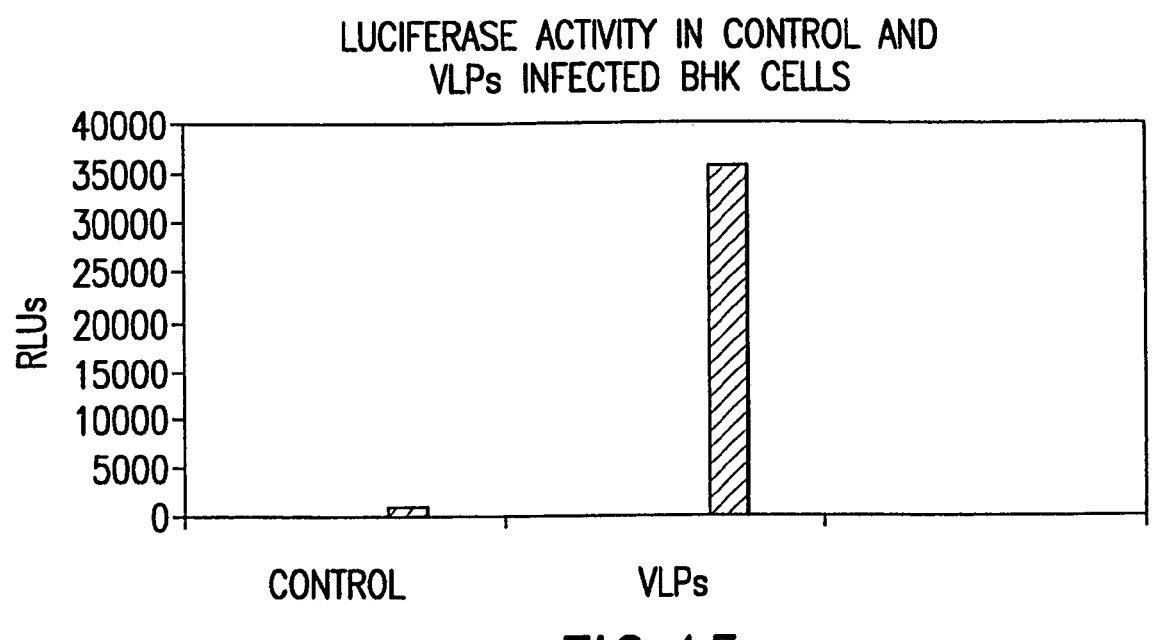
FIG. 15 depicts the measurement of luciferase activity in relative light units (RLUs) in uninfected (control) and VLP-infected baby hamster kidney cells (BHK).

To evaluate RNP formation and encapsidation, an in vitro minus sense RNA template encoding luciferase in anti-sense orientation was synthesized, flanked by the 3' and 5' conserved and non-coding regions of the influenza virus NP termini. Transfection of Sf9 insect cells with the in vitro generated RNA and subsequent co-infection with Q28 and the second quadruple recombinant led to the assembly and release of VLPs that carried the reporter gene as well as the polymerase and NP. Concentrated supernatants of transfected/infected Sf9 cells were transferred to a baby hamster kidney cell (BHK) monolayer, incubated, and the cells disrupted with a luciferase assay lysis buffer. Lysates of infected cells registered luciferase activity 70-700 times that of uninfected control cells (FIG. 15).

Figure 16:
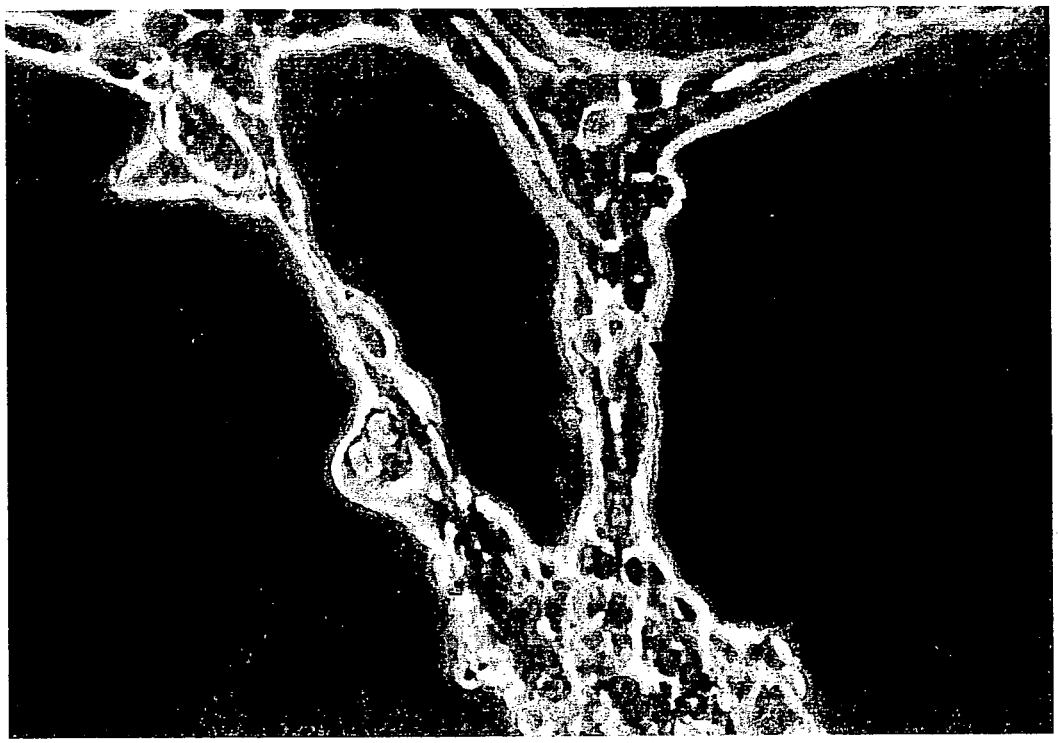
FIG. 16 depicts the expression of green fluorescence protein (GFP) in BHK cells following infection with VLPs carrying the GFP gene. Arrows indicate BHK cells which express GFP.

Similarly, to evaluate RNP formation and encapsidation, an in vitro minus sense RNA template encoding green fluorescence protein (GFP) in anti-sense orientation was synthesized, flanked by the 3' and 5' conserved and non-coding regions of the influenza virus NP termini. Transfection of Sf9 insect cells with the in vitro generated RNA and subsequent co-infection with Q28 and the second quadruple recombinant led to the assembly and release of VLPs that carried the reporter gene as well as the polymerase and NP. When concentrated supernatants of transfected/infected Sf9 cells were transferred to a MDCK cell monolayer, the expression of GFP was detected (FIG. 16).

These results indicate that the baculovirus-derived particles were able to encapsidate RNPs, which were functional in primary transcription, as demonstrated by the expression of luciferase and GFP. Thus, the VLPs are able to assemble and package RNPs, as well as to further incorporate and express a heterologous nucleotide sequence. Such an expressed heterologous sequence includes, but is not limited to a heterologous moiety not produced by influenza virus, including a peptide, polypeptide or protein from a non-influenza pathogenic microorganism, as described below. Such an-expressed heterologous sequence further includes an immune modulator to increase and/or shift the immune response. Such immune modulators include, but are not limited to, IL-12 (Genetics Institute, Cambridge, Mass.) and GM-CSF (Immunex Corp., Seattle, Wash.). Still further expressed heterologous sequences include monoclonal antibodies which serve as targeting and/or treatment moieties.

The VLPs of this invention are used to formulate immunogenic or pharmaceutical compositions. To do so, the VLPs are adjusted to an appropriate concentration and formulated with any suitable adjuvant, diluent or carrier. Physiologically acceptable media may be used as carriers and/or diluents. These include, but are not limited to: water, an appropriate isotonic medium, glycerol, ethanol and other conventional solvents, phosphate buffered saline and the like. Suitable adjuvants include, but are not limited to aluminum phosphate, aluminum hydroxide, MPL™ (3-O-deacylated monophosphoryl lipid A; RIBI ImmunoChem Research, Inc., Hamilton, Mont., now Corixa), synthetic lipid A analogs such as 529 (Corixa), Stimulon™ QS-21 (Aquila Biopharmaceuticals, Framingham, Mass.), IL-12 (Genetics Institute, Cambridge, Mass.), synthetic polynucleotides such as oligonucleotides containing a CpG motif (U.S. Pat. No. 6,207,646 (28)), the heat-labile toxin of *E. coli*, and cholera toxin (either in a wild-type or mutant form, for example, where the glutamic acid at amino acid position 29 is replaced by another amino acid, preferably a histidine, in accordance with published International Patent Application Number WO 00/18434 (29)).

In one embodiment of this invention, the formulation including the VLPs is intended for use as an immunogenic composition. The virus may be mixed with cryoprotective additives or stabilizers such as proteins (e.g., albumin, gelatin), sugars (e.g., sucrose, lactose, sorbitol), amino acids (e.g., sodium glutamate), saline, or other protective agents. This mixture is maintained in a liquid state, or is then dessicated or lyophilized for transport and storage and mixed with water immediately prior to administration.

Formulations comprising VLPs containing only influenza virus structural proteins are useful to immunize a human or other vertebrate subject to induce protection against infection by influenza virus. Thus, this invention further provides a method of immunizing a subject to induce protection against infection by influenza virus by administering to the subject an effective immunizing amount of a formulation of the immunogenic composition incorporating VLPs containing only influenza virus structural proteins, generated as described hereinabove.

Formulations comprising VLPs containing surface glycoproteins from different subtypes of influenza virus, such as HA from one subtype and NA from a different subtype, are formulated with a diluent or carrier as a bivalent immunogenic composition for immunizing vertebrates against infection caused by those two subtypes of influenza virus. As discussed above, each of HA and NA can be replaced as antigenic variants are identified. Thus, updated chimeric VLPs are readily constructed in accordance with the methods described herein.

Alternatively, multivalent immunogenic compositions are prepared by generating one set of VLPs from each influenza strain of interest, mixing the sets of VLPs in appropriate ratios, and administering the resulting immunogenic composition.

Formulations of this invention also comprise VLPs where a portion or all of the HA or NA is replaced by a heterologous moiety not produced by influenza virus, so as to comprise chimeric VLPs. Such moieties include, but are not limited to, a peptide, polypeptide or protein. Where only a portion of the HA or NA is to be replaced, a portion of the DNA sequence in the recombinant DNA molecule which encodes the HA or NA is replaced by a DNA sequence which encodes the non-influenza peptide, polypeptide or protein. Where the entire HA or NA is to be replaced, the entire DNA sequence in the recombinant DNA molecule which encodes the HA or NA is replaced by a DNA sequence which encodes the non-influenza peptide, polypeptide or protein Alternatively, a heterologous moiety as described above which is not produced by influenza virus (or an influenza virus segment such as that encoding NP) is incorporated within the VLPs. This is achieved by co-infecting, co-transfecting or otherwise co-transforming a suitable host cell with: (a) one or more recombinant DNA molecules which each encode at least one influenza virus structural protein, where a recombinant DNA molecule encoding M1 is always constructed, and (b) a recombinant DNA molecule which encodes the heterologous moiety (or influenza virus segment), culturing the host cell under conditions which permit the expression of said at least one influenza virus structural protein, so that VLPs are assembled within the cells after expression of the at least one influenza virus structural protein, and purifying the VLPs from the culture supernatant. The heterologous moiety (or influenza protein) is incorporated within the VLPs.

Where such non-influenza peptide, polypeptide or protein is from a pathogenic microorganism, the resulting chimeric VLPs are formulated with a diluent or carrier as an immunogenic composition for immunizing vertebrates against infection caused by that pathogenic microorganism (as well as influenza virus). Most typically, the chimeric VLP includes a surface antigen from a non-influenza pathogenic microorganism.

Such non-influenza pathogenic microorganisms include, but are not limited to, those from viruses, bacteria, fungi or parasitic microorganisms which infect humans and non-human vertebrates. Other types of non-influenza moieties include, but are not limited to, those from cancer cells or tumor cells, monoclonal antibodies (used, for example, as targeting and/or treatment moieties), allergens, amyloid peptide protein, or other macromolecular components.

Examples of such viruses include, but are not limited to, Human immunodeficiency virus, Simian immunodeficiency virus, Respiratory syncytial virus, Parainfluenza virus types 1-3, Herpes simplex virus, Human cytomegalovirus, Hepatitis A virus, Hepatitis B virus, Hepatitis C virus, Human papillomavirus, poliovirus, rotavirus, caliciviruses, Measles virus, Mumps virus, Rubella virus, adenovirus, rabies virus, canine distemper virus, rinderpest virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses.

Examples of such bacteria include, but are not limited to, *Haemophilus influenzae* (both typable and nontypable), *Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium intracellulare* complex, *Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum.*

Examples of such fungi include, but are not limited to, *Aspergillis, Blastomyces, Candida, Coccidiodes, Cryptococcus* and *Histoplasma.*

Examples of such parasites include, but are not limited to, *Leishmania major, Ascaris, Trichuris, Giardia, Schistosoma, Cryptosporidium, Trichomonas, Toxoplasma gondii* and *Pneumocystis carinii.*

Examples of such cancer cells or tumor cells include, but are not limited to, prostate specific antigen, carcino-embryonic antigen, MUC-1, Her2, CA-125 and MAGE-3.

Examples of such allergens include, but are not limited to, those described in U.S. Pat. No. 5,830,877 (30) and published International Patent Application Number WO 99/51259 (31), which are hereby incorporated by reference, and include pollen, insect venoms, animal dander, fungal spores and drugs (such as penicillin). Such components interfere with the production of IgE antibodies, a known cause of allergic reactions.

Amyloid peptide protein (APP) has been implicated in diseases referred to variously as Alzheimer's disease, amyloidosis or amyloidogenic disease. The β-amyloid peptide (also referred to as Aβ peptide) is a 42 amino acid fragment of APP, which is generated by processing of APP by the β and γ secretase enzymes, and has the following sequence: ASP Ala Glu Phe Arg His Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala (SEQ ID NO:2).

In some patients, the amyloid deposit takes the form of an aggregated Aβ peptide. Surprisingly, it has now been found that administration of isolated Aβ peptide induces an immune response against the Aβ peptide component of an amyloid deposit in a vertebrate host (32). Such Aβ peptides have also been linked to unrelated moieties. Thus, the VLPs of this invention include the expression of this Aβ peptide in lieu of a portion or all of the HA or NA of influenza virus, as well as fragments of Aβ peptide and antibodies to Aβ peptide or fragments thereof. One such fragment of Aβ peptide is the 28 amino acid peptide having the following sequence (33): ASP Ala Glu Phe Arg His Asp Ser Gly Tyr Glu Val His His Gln Lys Leu Val Phe Phe Ala Glu Asp Val Gly Ser Asn Lys (SEQ ID NO:3).

A sufficient amount of an above-described immunogenic composition in an appropriate number of doses is administered to the subject to elicit an immune response. Persons skilled in the art will readily be able to determine such amounts and dosages. Administration may be by any conventional effective form, such as intranasally, parenterally, orally, or topically applied to any mucosal surface such as intranasal, oral, eye, lung, vaginal or rectal surface, such as by an aerosol spray. The preferred means of administration is by intranasal administration.

Such non-influenza peptide, polypeptide or protein can also be a pharmaceutically active moiety. Such moieties include, but are not limited to, therapeutic proteins, growth factors, immune modulators, monoclonal antibodies, as well as the moieties listed above with regard to the immunogenic compositions. These chimeric VLPs are formulated with a diluent or carrier as discussed above as a pharmaceutical composition and administered in an amount effective for treating vertebrates with said such non-influenza peptide, polypeptide or protein. An effective amount is readily determined by persons skilled in the art.

The foregoing pharmaceutical compositions may further comprise an adjuvant as discussed above.

Such non-influenza peptide, polypeptide or protein can also be a receptor or ligand useful in receptor-ligand studies. For example, a non-influenza glycoprotein is included in VLPs which is targeted to a specific receptor.

In all of these immunogenic or pharmaceutical compositions, the VLPs are capable of inducing an immune response when admininstered to a vertebrate host, but are not capable of causing disease symptoms because VLPs contain no genetic material and cannot replicate in the vertebrate subject.

All patents and publications cited herein are hereby incorporated by reference.

In order that this invention may be better understood, the following examples are set forth. The examples are for the purpose of illustration only and are not to be construed as limiting the scope of the invention.

EXAMPLES

Example 1

Cloning of Influenza M2 Gene into the Baculovirus Transfer Vector pAcAB4

The influenza M2 gene, which is a spliced product of the M1 mRNA, was isolated by RT-PCR from polyadenylated mRNA extracted from MDCK cells which had been infected with the influenza A/Udorn/72 (H3N2) strain. The M2 gene was cloned as a DNA insert into a pGemT vector (Promega) and sequenced with specific primers using a dye termination sequencing reaction and an automated ABI 377 DNA sequencer (Applied Biosystems).

The M2 gene was released from the pGemT-M2 plasmid by digestion with the EagI restriction enzyme and prepared for cloning into the pAcAB4 (PharMingen) baculovirus transfer vector. The M2-DNA fragments were filled in with DNA polymerase (Klenow fragment) and BglII linkers were incorporated into the termini by ligation with T4 DNA ligase. All enzymes and linkers were obtained from New England Biolabs (NEB). Transfer vector pAcAB4 was then digested with BglII and treated with calf intestinal alkaline phosphatase (CIP). The M2 insert was then gel purified (Qiagen) and ligated into the transfer vector at a 3:1 ratio. A positive clone was selected by restriction analysis and plasmid DNA was prepared from a 100 ml *E. coli* culture using Qiagen Plasmid purification kits. This construct will now be referred to as pAcAB4/M2.

Example 2

Construction of an Intermediate ("Shuttle") Vector

Due to limitations in the number of convenient restriction sites to clone influenza genes into the transfer vector pAcAB4, a shuttle cloning vector was generated carrying three baculovirus promoters (two polyhedrin and one p10) flanked by new restriction sites that were added by PCR. This shuttle vector was constructed as follows: pAcAB4M2. (from Example 1) was digested with SmaI and divided into two samples. One pAcAB4/M2-SmaI sample was digested with XbaI, which released a 400 nucleotide long DNA fragment. This DNA was gel purified and amplified by PCR with two primers, one of which incorporated into one end of the final product the PmeI (italics) and NotI (underlined) sites:

```
                                           (SEQ ID NO:4)
5' GTTTAAACGCGGCCGCCGTATTTATAGGTTTTTTTATTA 3'

(SEQ ID NO:5)
5' TTTTATTACTAGTCCCGGGGATCTGTGATTGTAAAT 3'
```

The other pAcAB4/M2-SmaI sample was digested with BamHI, and the released SmaI/BamHI DNA fragment was gel purified and also amplified by PCR with two primers, one of which incorporated into the final PCR product the SacI (italics) and NheI (underlined) sites:

```
                                           (SEQ ID NO:6)
5' AAGAGCTCGCTAGCGTATTTATAGGTTTTTTTATTA 3'

(SEQ ID NO:7)
5' ACAATCACAGATCCCCGGGACTAGTAATAAAACCTAGA 3'
```

These two PCR products, which overlap at the unmodified termini, were used in another PCR reaction with two external primers specific for the newly incorporated restriction enzyme sites: 5' GTTTAAACGCGGCCGCCG 3' (SEQ ID NO:8) 5' AAGAGCTCGCTAGCGTA 3' (SEQ ID NO:9)

This PCR DNA was then digested with SacI/PmeI. The pNEB193 plasmid (Promega) was also digested with SacI/PmeI and ligated with the digested PCR DNA with T4 ligase. Finally, this resultant pNEB193 shuttle vector carries a DNA fragment containing two polyhedrin promoters and one p10 promoter flanked by new restriction sites that are used in the subsequent cloning of the influenza genes HA, NA, and M1.

Example 3

Cloning of Influenza HA, MA and M1 Genes into the Shuttle Vector

The influenza genes HA, NA, and matrix (M1) were recovered by RT-PCR from purified genomic RNA of influenza virus A/Udorn/72 (H3N2). All three genes were cloned as DNA inserts into pGemT or pGemTeasy vectors (Promega) and sequenced with specific primers using a: dye termination sequencing reaction and an automated ABI 377 DNA sequencer. The two donor splice sites at the 5' end of the M1 gene were mutated using a QuikChange Kit from Stratagene (pGT-M1 splice) to prevent the potential splicing of the M1 mRNA in host cells.

These three genes were cloned into the shuttle vector in three steps:

1) Cloning of M1 Gene:

The pGemT/M1 (splice) plasmid (pGemT carrying the M1 gene) was used as the template in a PCR reaction with 5' and 3' primers that introduced an NheI and an SacI site, respectively, in the amplified DNA. This PCR DNA was then digested with NheI/SacI and gel purified. Similarly, the pNEB193 shuttle vector was digested with NheI/SacI and purified. The shuttle vector and insert (M1 PCR) were ligated and amplified in *E. coli* following transfection. The M1 gene was sequenced using BigDye (Perkin Elmer). The M1 gene was positioned downstream from the polyhedrin promoter. The resulting plasmid was called pNEB193M1.

2) Cloning of HA Gene:

The pGemT/HA plasmid (pGemT carrying the HA gene) was digested with SacII and end filled. NotI linkers were ligated onto the digested DNA. The DNA was then digested with NotI so that the HA insert would be released and have NotI sites on each end. The plasmid pNEB193M1 was digested with NotI, treated with calf intestinal phosphatase (CIP) and the HA insert was ligated into it with T4 DNA ligase (not directional). PCR was used to determine the orientation of the HA gene, which is under the transcriptional control of the polydedrin promoter. The resulting plasmid was called pNEB193M1/HA.

3) Cloning of NA Gene:

The plasmid pGemT/NA3B (pGemT carrying the NA gene) was first digested with SacII and end filled with T4 DNA polymerase. Subsequently, the NA gene was released by digestion with SpeI and filled in with Klenow, and the NA insert was blunt-end ligated. Next, pNEB193M1/HA was digested with SmaI, and the NA insert was blunt-end ligated. PCR was used to identify the clone that carried the NA gene in the correct orientation. The NA gene was positioned downstream from the p10 promoter. The resulting plasmid was called pNEB193M1/HA/NA.

Example 4

Construction of a Transfer Vector Containing Influenza Genes M2, M1, HA and NA After the completion of the process described in Example 3, the pNEB193M1/HA/NA shuttle vector contained the M1, HA, and NA genes positioned under the transcription regulatory control of baculovirus promoters. To release these three genes as a single piece of DNA, the shuttle vector was digested with PmeI/SacI. This DNA fragment was ligated into pAcAB4M2 from Example 1 (which already contained the M2 gene), which had been modified as follows: New restriction sites were introduced into the pAcAB4/M2 to facilitate the cloning of the DNA fragment containing these three genes from the shuttle vector. This pAcAB4/M2 plasmid was then digested with XbaI, termini filled-in with DNA polymerase (Klenow fragment) and PmeI linkers added with T4 DNA ligase. This DNA was then digested with PmeI and religated to regenerate the PmeI site. Similarly, the religated plasmid was digested with BamHI, filled-in with DNA Polymerase (Klenow) and SacI linkers were attached with T4 ligase. Subsequent digestion with SacI and ligation restored the SacI site. The resulting pAcAB4/M2 vector has two new sites, PmeI and SacI. The vector was prepared for the insertion of the additional influenza genes by digestion with PmeI/SacI and gel purification. All junctions were sequenced to make certain that no mutations were introduced during the pNEB193 cloning. The resulting construct was designated HA/Q (see FIG. 1), which is a transfer vector carrying four influenza genes (pAcAB4/M2/M1/HA/NA).

Example 5

Generation of Chimeric Transfer Vectors

The coding sequence for the VSV G protein was recovered from the VSV by RT-PCR of viral RNA with specific primers to the 3' and 5' ends of the G gene (5' AACAGAGATCGATCTGT 3' and (SEQ ID NO:10)

5' CATAAAAATTAAAAATTAAAATATAATTAAGG 3') (SEQ ID NO:11)

and cloned into pGemT plasmid (Promega). The resulting pGemT-VSV clone was digested with SacII and blunt-ended with T4 DNA Polymerase. It was then digested with SpeI and end-filled with Klenow. NotI linkers were added with T4 ligase and then redigested with NotI. Subsequently, the VSV G coding sequence was ligated into the Q28 vector which had been digested with NotI to remove the HA gene. Orientation of the gene was confirmed by PCR and sequencing. This construct was designated transfer vector VSV-G.

In an alternative embodiment, only a portion of the VSV G gene was inserted. A chimeric gene (see FIG. 2) containing the ectodomain of G protein fused in frame with the transmembrane (29 amino acids) and cytoplasmic (14 amino acids) domains of HA was generated by PCR as follows: The transmembrane domain and cytoplasmic tail of the influenza HA gene were amplified from the pGemT-HA clone by PCR and gel purified. The ectodomain of the VSV G gene was also amplified by PCR and gel purified. Both of these DNA fragments were used as templates in a PCR reaction with Pfu DNA polymerase (Stratagene, LaJolla, Calif.) using a primer corresponding to the 5' end of the VSV G gene and the 3' end of the HA gene. A 1620 bp DNA fragment was gel purified and NotI linkers were added with T4 ligase, followed by digestion with NotI. This insert was ligated into the HA/Q vector that had been digested with NotI to remove the HA gene. The resultant construct generated the transfer vector VSV-G/HA (chimera).

Example 6

Transfection of Quadruple Baculovirus Recombinants in Insect Cells

Sf9 cells (ATCC CRL 1711) were seeded onto 60 mm dishes at a density of $2 \times 10^6$ cells per dish. Approximately 2 μg of HA/Q transfer vector were mixed with 0.5 μg of linearized BaculoGold DNA (PharMingen) and Sf9 cells were transfected with the DNA using the BaculoGold Transfection Kit (Pharmingen). Recombinant baculoviruses were selected and purified by three rounds of plaque purification. One such plaque purified recombinant was designated HA/Q28 and was selected for further studies.

In addition, the quadruple transfer vector DNA carrying a full length VSV-G or a VSV-G/HA (chimera) was transfected with linearized BaculoGold DNA into Sf9 cells as described above to generate the recombinants VSV-G/Q and VSV-G/HA/Q. Recombinant viruses were selected as described above for HA/Q28. All recombinants were amplified in Sf9 cells to a titer of $7\times10^7$ pfu/ml.

Example 7

Growth of Sf9 Insect Cells and Infection with Baculovirus Recombinants

All Sf9 cell cultures were grown in suspension in serum-free media. Infections with baculovirus recombinants were carried out at a multiplicity of infection (MOI) of 5. Recombinant viruses were inoculated into the cell monolayers in a small volume, allowed to adsorb for 30 minutes at room temperature and then incubated at 28° C. after adding serum-free fresh media. Cells and culture media were collected 72 hours post-infection, unless otherwise specified, and used for subsequent analysis of expression of proteins and formation of VLPs.

Example 8

Cloning of Single Influenza Genes into the Transfer Vector pBlueBac4.5 and Generation of Single Baculovirus Recombinants The M1 gene of influenza A/Udorn was previously cloned into pGemT (pGT-M1 splice, see Example 1 above). To subclone the M1 gene, pGT-M1 was digested with SacII, blunt-ended with T4 DNA polymerase, and SacI linkers were added to the ends with T4 ligase. The plasmid was then digested with SacI/SalI and the released M1 was gel purified. The insert was ligated into pBlueBac4.5 (Invitrogen), which had been digested with SacI/SalI, and DH5α cells were transformed with the ligation mix.

To subclone the HA gene into pBlueBac4.5, pGemT/HA (see Example 3 above) was digested with SacII and blunt-ended with T4 DNA Polymerase. The DNA was then redigested with SalI to remove the insert and was gel purified. The HA insert was ligated into NheI(blunt)/SalI-digested pBlueBac 4.5, and STBL2 competent *E. coli* cells were transformed with the ligation mix.

The pGemT-NA (see Example 3 above) was digested with SacII and blunt-ended with T4 DNA Polymerase. This DNA was then digested with SpeI and gel purified. The insert was ligated into a pBlueBac4.5 vector that had been digested with NheI/SmaI, and STBL2 competent *E. coli* cells were transformed.

When the transfer vector DNA was found to be correct by sequencing, Sf9 cells were transfected with 5 μg of each pBlueBac clone and 10 μg of Bac & Blue DNA (Invitrogen). The Sf9 cells were cotransfected with these DNAs by liposome-mediated transfection. The cells were incubated for five days and the supernatant was plaque purified. Single blue plaques were grown and amplified in Sf9 cells and protein expression was evaluated by Western Blots. The NP baculovirus recombinant (containing the influenza NP gene) used in this work was constructed as described by Galarza et al. (27).

Example 9

Immunoblotting Analysis

Western blot analysis was used to identify proteins in infected Sf9 cells, concentrated supernatants and gradient fractions. Samples were resolved on a 10% SDS-PAGE gel (unless otherwise specified) and transferred onto a nitrocellulose membrane. Blots were blocked in a solution of TBS (tris-buffered saline) containing 5% nonfat dry milk and 0.1% Tween-20, and subsequently probed with a mixture of monoclonal antibodies to the influenza HA, M1 (matrix) and M2 proteins. The mouse monoclonal anti-HA (clone 12CA5) was obtained from Roche Molecular Biochemicals (Indianapolis, Ind.). Mouse monoclonal anti-M1 (clone GA2B) was from Serotec (Raleigh, N.C.). Mouse monoclonal anti-M2 was from Mt. Sinai Hybridoma Center (New York, N.Y.). Antigens were visualized on western blots with an alkaline phosphatase-conjugated anti-mouse IgG secondary antibody (Promega). Analyses of VLP formation in Sf9 cells infected with a mono, double or triple combination of single gene baculovirus recombinants were carried out in a similar fashion. Analysis of samples containing the VSV G protein were probed with a mouse monoclonal anti-G antibody (clone P5D4; Roche Molecular Biochemicals) in combination with the antibodies to the influenza M1 and M2 proteins. The results are shown in FIG. 3.

Example 10

Immunoflourescence of Infected Sf9 Cells

Sf9 cells were grown in eight square-chamber (box cultures) and infected with quadruple or single gene baculovirus recombinants at an MOI of 1. At 72 hours post-infection, individual boxes of Sf9 cells were fixed in either methanol/acetone (2:1) or 3% paraformaldehyde. As a blocking step, fixed cells were incubated for 30 minutes at room temperature in phosphate-buffered saline (PBS) containing 3% bovine serum albumin (BSA). Subsequently, each slide was incubated sequentially with a solution of primary and secondary antibodies. A combination of rat anti-HA (Roche Molecular Biochemicals)/mouse anti-M1 monoclonal (see Example 9) antibodies (as primary, dilution 1:100) and a combination of goat anti-rat rhodamine conjugated (Molecular Probes)/sheep anti-mouse FITC conjugated (Sigma) antibodies (as secondary) were used to examine expression of HA and M1. A combination of rat monoclonal anti-HA/rabbit anti-NA peptides (custom-made by Research Genetics) (as primary, dilution 1:100) and goat anti-rat rhodamine conjugated (Molecular Probes)/sheep anti-rabbit FITC conjugated (Sigma) antibodies (as secondary) were used to examine expression of NA and HA. As an alternative to rhodamine, a Cy3-conjugated goat anti-rat (Sigma) antibody may be used. Each antibody reaction was incubated for 30 minutes at room temperature and, between steps, slides were rinsed three times with PBS. The FITC and rhodamine molecules emitted green and red light respectively when excited at wavelengths of 495 nm and 552 nm, which were discriminated with appropriate filters. The results of the immunofluorescence analyses are shown in FIGS. 4-7.

Example 11

Purification of Influenza VLPs

Sf9 cells were seeded at a density of $7.5 \times 10^7$ cells per 150 cm² tissue culture flask and allowed to settle at room temperature for 30 minutes. Cells were infected with baculovirus recombinants (HA/Q28, VSV-G/Q, VSV-G/HA/Q chimera or single recombinant) at an MOI of 5 and infection was allowed to proceed for 72 hours at 28° C. When complete, the culture medium was harvested and subjected to low speed centrifugation (30 minutes at 4° C. and 2000×g). The supernatant was then pelleted by spinning at 200000×g for 90 minutes. Depending on the number of cells initially infected, the resulting pellets were resuspended in 50 µl or 500 µl of 1×PBS, homogenized by a brief sonication and then loaded on top of an Iodixanol (Optiprep, Nycomed/Sigma) gradient (density of 1.08 g/ml to 1.32 g/ml). The gradient was spun at 200000×g for 3.5 hours and fractions were collected by gravity from the bottom of the tube using a U-shape micro-capillary tube. Aliquots of these fractions were analyzed by western blot after SDS-PAGE. The western blots are shown in FIGS. 8 and 9. To further purify the particles, fractions containing the VLPs were subjected to a second sucrose gradient centrifugation. For sucrose equilibrium gradient centrifugation, the previously selected fraction was. dialyzed with PBS and layered onto a 20-60% (wt/wt) sucrose (in NTE) gradient and centrifuged for 22 hours at 4° C. and 150000×g. After centrifugation, 0.5 ml fractions were collected from the bottom of the tube, as described above, and analyzed by western blot after SDS-PAGE.

The fractions containing the VLPs were then examined by electron microscopy and immunogold labeling (see Example 12).

Example 12

Electron Microscopy: Negative Staining and Immunogold Labeling

For negative staining and immunogold labeling, VLPs were concentrated from culture supernatant and purified by two consecutive density gradient centrifugations (see Example 11). Aliquots of the samples were placed on fresh glow discharged plastic/carbon-coated grids, washed gently with a few drops of distilled water, negative stained with 2% sodium phosphotungstate, pH 6.5, and viewed with an electron microscope. An electron micrograph of negatively stained influenza VLPs is depicted in FIG. 10.

Samples for immunogold labeling of the surface antigens decorating the VLPs were prefixed in 0.5% glutaraldehyde for five minutes, placed on the grids as described above and washed with a few drops of distilled water. Subsequently, they were sequentially incubated facedown on top of 100 µl volumes of the following solutions: primary antibodies diluted in PBS-1% BSA for 30 minutes; three times with PBS-1% BSA for five minutes each; suspension of gold spheres coated with antibody against mouse IgG-diluted in PBS-1% BSA (1:10) for 30 minutes; three times with PBS-1% BSA, for five minutes each. Finally, they were washed with a few drops of distilled water, stained with 2% uranyl acetate, air-dried and examined in the electron microscope. Electron micrographs of immunogold labeled influenza VLPs probed with anti-HA or anti-NA monoclonal antibodies and counterstained with gold spheres coupled to anti-mouse IgG are depicted in FIG. 11.

Example 13

Incorporation of Influenza Nucleoprotein (NP) into VLPs

Sf9 cells were co-infected with either HA/Q28 and NP or NP and M1 single baculovirus recombinants. Concentrated supernatants of the co-infected cells were purified in accordance with Example 11. A western blot of the fraction containing both HA and NP as expressed by these co-infected cells is depicted in FIG. 9B. A western blot of the fraction containing NP and M1 as expressed by these co-infected cells is depicted in FIG. 8C.

Example 14

Immunogenicity of VLPs in Mice

Figure 12B:
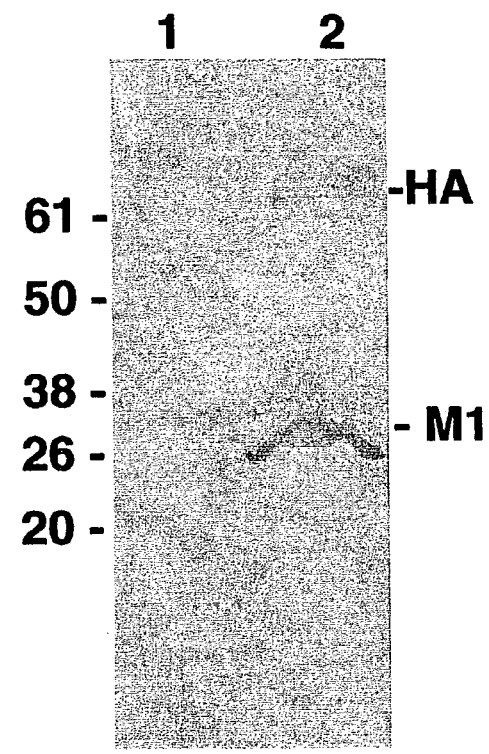
In FIG. 12B, results are depicted from pooled sera from a second pair of two mice. In each of FIGS. 12A and B, Lane 1: uninfected MDCK cells as control; lane 2: influenza A virus infected-MDCK cells. Probing of uninfected MDCK cells showed a nonspecific band slightly above that of M1, which was also present in influenza-infected cells.

Two groups of Balb/c mice (4-5 weeks old) were immunized via the intramuscular route with either HA/Q28 VLPs (approximately 1 µg HA) or VSV-G/Q VLPs (approximately 1 µg G), where each set of VLPs was formulated with aluminum phosphate (200 µg/dose). All mice in each group received a primer and two booster injections at two-week intervals. Two weeks after the last immunization, blood samples were obtained and the presence of antibodies against the corresponding antigen were evaluated by western blot (for both types of VLPs), inhibition of hemagglutination assay (IHA) (for the HA/Q28) and a serum neutralization test (for VSV-G/Q). Western blots are depicted in FIG. 12 (for HA/Q28) and FIG. 13 (for VSV-G/Q). IHA titers were measured in IHA units (IHAU) and were as follows:

| | |
|---|---|
| Naïve mice: | 32 IHAU* |
| Positive control: | 128 IHAU |
| [influenza A/Hong Kong] | |
| HA/Q28 pooled sera: | 96 IHAU |

*Naïve mice showed an inhibition titer, which may be due to nonspecific agglutinins. All samples were treated with kaolin and heated at 56° C. for 30 minutes in an effort to inactivate nonspecific inhibitors and/or nonspecific agglutinins.

For the serum neutralization test, increasing dilutions of sera of mice immunized with VSV-G/Q were placed atop a cell monolayer containing VSV, incubated and analyzed for the ability to inhibit virus, as seen by the prevention of the formation of any plaques in the cell monolayer. It was found that a dilution as high as 1/64 of the sera completely neutralized a standard titer of VSV (1×10⁶ PFU/ml).

Example 15

Packaging of Ribonucleoprotein Complexes (RNPs) into Influenza VLPs and Expression of Reporter Genes Polymerase (Subunits PB1, PB2 and PA) and NP Baculovirus Contruct (Quadruple Transfer Vector Recombinant)

The three genes encoding the subunits of the polymerase (PB1, PB2, and PA proteins) and the nucleoprotein NP of the influenza virus A/Udorn/72 (H3N2) strain were subcloned into a single baculovirus transfer vector PAcAB4. The PB1 and PA genes were positioned in opposite orientations under the transcriptional control of the baculovirus polyhedrin promoter, whereas the PB2 and NP genes, also in opposite orientations, were under the transcriptional control of the baculovirus p10 promoter. Co-transfection of Sf9 insect cells with purified transfer vector DNA, which carries the polymerase genes and NP, and linearized-genomic baculovirus DNA, allowed for homologous recombination. This resulted in the transfer of the polymerase and NP genes into the baculovirus DNA. This intracellular recombination event generated the quadruple-baculovirus recombinant (FIG. 14) that was released into the culture medium. Three consecutive plaque purification/amplification steps were carried out to select quadruple baculovirus transfer vector recombinants. PCR using gene specific primers was performed to confirm the presence of the four genes in the purified quadruple recombinants. Western blot assays with anti-PB1, anti-PB2, anti-PA and anti-NP specific polyclonal antibodies were performed to evaluate the expression of the three polymerase subunits and NP (data not shown).

Reporter Gene Constructs

DNA plasmids were generated which contained the luciferase or the green fluorescence protein (GFP) genes flanked by the conserved 3' and 5' termini of influenza virus. These sequences are required for the transcription/replication and packaging of the influenza genome in a wild-type virus infection. In addition to the conserved sequences, precise 3' and 5' termini are essential for a functional genome. In order to obtain these precise ends, an altered T7 promoter was added to the 5' terminus of the influenza sequence; thereafter, transcription with T7 RNA polymerase generated precise influenza 5' termini in the RNA transcripts. In addition, a BsaI restriction site was engineered at the 3' end of the influenza sequence. Digestion of the plasmid with this restriction enzyme produced DNA templates with 5' overhang, which in run-off T7 RNA polymerase transcription reactions, generated RNA molecules with precise influenza 3' termini. These model influenza reporter genes were then used to study polymerase activity, RNA encapsidation, and packaging of RNA into influenza virus-like particles.

VLP Packaging of Luciferase Reporter Gene

Sf9 insect cells were simultaneously infected (MOI: 5) with the Q28 (HA, NA, M1, M2), and quadruple transfer (PB1, PB2, PA, NP) vector baculovirus recombinants. Infection was allowed to proceed for 48 hours and at that time, 30 ug of an in vitro synthesized RNA containing the luciferase gene in reverse orientation flanked by the 3' and 5' termini sequences of the influenza genome, was transfected into Sf9 cells using the LT1 transfection reagent (Panvera, Madison, Wis.). Infected/transfected cells were incubated for an additional 24 hours. The culture supernatant was then harvested, clarified by slow speed centrifugation, and VLPs concentrated by centrifugation for two hours at 2000×g. VLPs were resuspended in culture medium and applied onto a new monolayer of baby hamster kidney cells (BHK). After 48 hours of incubation, BHK cells were disrupted with luciferase assay lysis buffer, and luciferase activity measured in the cell extract. Background luciferase activity was determined in uninfected BHK cells (control) using a luminometer and the readings ranged from 50 to 500 relative light units (RLUs). Lysates of VLP-infected BHK cells registered a luciferase activity reading of 36,000 RLUs (FIG. 15).

VLP Packaging of Green Fluorescence Protein (GFP) Reporter Gene

Similar packaging experiments of RNPs into VLPs were performed using the green fluorescence protein gene (GFP) as a reporter. Sf9 insect cells were infected/transfected following the parameters described above. Transfected RNA molecules were constructed which contained the coding sequence for the GFP in an anti-sense orientation flanked by the 3' and 5' termini of the influenza viral RNA. BHK cells and MDCK cells were infected for 24 hours with VLPs and the expression of GFP was then monitored using a Zeiss microscope and fluorescein isothiocyanate (FITC) filters. A small number of green cells were present, suggesting that the VLPs were able to transfer the GFP gene, thereby resulting in the expression of green fluorescence protein (FIG. 16).

BIBLIOGRAPHY

1. Lamb, R. A., pages 1-87 of *The Influenza Viruses*, R. M. Krug, ed. (Plenum Press, 1989).
2. Lamb, R. A., et al., *Cell*, 40, 627-633 (1985).
3. Martin, K., and Helenius, A., *Cell*, 67, 117-130 (1991).
4. Shapiro, G. I., et al., *J. Virology*, 61, 764-773 (1987).
5. Garoff, B., et al., *Microbiology and Molecular Biology Reviews*, 62, 1171-1190 (1998).
6. Nayak, D. P., *ASM News*, 62, 411-414 (1996).
7. Justice, P. A., et al., *J. Virol.*, 69, 3156-3160 (1995).
8. Li, Y., et al., *J. Virol.*, 67, 4415-4420 (1993).
9. Mebatsion, T., et al., *Cell*, 84, 941-951 (1996).
10. Coronel, E. C., et al., *J. Virol.*, 73, 7035-7038 (1999).
11. Zhao, H., et al., *J. Gen. Virol.*, 79, 2435-2446 (1998).
12. Jin, H., *EMBO J.*, 13, 5504-5515 (1994).
13. Jin, E., et al., *EMBO J.*, 16, 1236-1247 (1997).
14. Zhang, J., et al., *J. Virology*, 74, 4634-4644 (2000).
15. Ruigrok, R. W. H., et al., *Virology*, 267, 289-298 (2000).
16. Roberts, P. C., et al., *Virology*, 240, 127-137 (1998).
17. U.S. Pat. No. 5,298,244.
18. Kirnbauer, R., et al., *Proc. Natl. Acad. Sci. USA.*, 89, 12180-12184 (1992).
19. Loudon, P. T., and Roy, P., *Virology*, 180, 798-802 (1991).
20. Rose, R. C., et al., *J. Virology*, 67, 1936-1944 (1993).
21. Zeng, C. Q.-Y., et al., *J. Virology*, 70, 2736-2742 (1996).
22. Gheysen, D., et al., *Cell*, 59, 103-112 (1989).
23. Nermut, M. V., et al., *Virology*, 198, 288-296 (1994).
24. Takahashi, H., et al., *Virology*. 256:371-380 (1999).
25. Yamshchikov, G. V., et al., *Virology*, 214, 50-58 (1995).
26. Ford, T., et al., *Analytical Biochem.*, 220, 360-366 (1994).
27. Galarza, J. M., et al., *Virus Res.*, 24, 91-106 (1992).
28. U.S. Pat. No. 6,207,646.
29. Published International Patent Application Number WO 00/18434.

30. U.S. Pat. No. 5,830,877.
31. Published International Patent Application Number WO 99/51259.
32. Published International Patent Application Number WO 99/27944.
33. U.S. Pat. No. 4,666,829.

What is claimed is:

1. A method of production of influenza virus-like particles (VLPs), said method consisting of the steps of:
   (i) constructing a recombinant DNA molecule which in terms of influenza virus proteins encodes only the influenza virus matrix structural protein (M1);
   (ii) constructing one or more recombinant DNA molecules which each encode at least one of but no more than all of the influenza virus structural proteins selected from the group consisting of hemagglutinin (HA), neuraminidase (NA) and the spliced product of M1 mRNA (M2);
   (iii) transfecting, infecting or otherwise transforming a suitable host cell with said recombinant DNA molecules referred to under (i) and with the recombinant DNA molecules referred to under (ii), culturing the host cell under conditions which permit the expression of said influenza virus structural proteins, so that VLPs are assembled within the cells after expression of the influenza virus structural proteins; and
   (iv) purifying the VLPs from the culture supernatant.

2. The method of claim 1 where HA and NA are from different subtypes of influenza virus.

3. A method of production of chimeric influenza virus-like particles (VLPs), said method consisting of the steps of:
   (i) constructing a recombinant DNA molecule which in terms of influenza virus proteins encodes only the influenza virus matrix structural protein (M1);
   (ii) constructing one or more recombinant DNA molecules which each encode at least one of but no more than all of the influenza virus structural proteins selected from the group consisting of hemagglutinin (HA), neuraminidase (NA) and the spliced product of M1 mRNA (M2), except wherein a portion or all of the HA or NA DNA sequences have been replaced by a DNA sequence which encodes a non-influenza moiety;
   (iii) transfecting, infecting or otherwise transforming a suitable host cell with the recombinant DNA molecules referred under (i) and with the recombinant DNA molecules referred to under (ii), culturing the host cell under conditions which permit the expression of said influenza virus structural proteins so that VLPs are assembled within the cells after expression of the influenza virus structural proteins; and
   (iv) purifying the VLPs from the culture supernatant.

4. The method of claim 3 where the DNA sequence in the recombinant DNA molecule which encodes the HA is replaced by a DNA sequence which encodes the G protein of Vesicular stomatitis virus (VSV).

5. The method of claim 3 where the DNA sequence in one recombinant DNA molecule encodes the transmembrane and cytoplasmic domains of HA, but the remaining coding region of HA is replaced by a DNA sequence which encodes the ectodomain of the G protein of VSV.

6. A method of production of influenza virus-like particles (VLPs), said method consisting of the steps of:
   (i) constructing a recombinant DNA molecule which in terms of the influenza virus protein encodes only the influenza virus matrix structural protein (M1);
   (ii) constructing one or more recombinant DNA molecules which each encode at least one of but no more than all of the influenza virus structural proteins selected from the group consisting of hemagglutinin (HA), neuraminidase (NA) and the spliced product of M1 mRNA (M2);
   (iii) transfecting, infecting or otherwise transforming a suitable host cell with the recombinant DNA molecules referred to under (i) and with the recombinant DNA molecules referred to under (ii), culturing the host cell under conditions which permit the expression of said influenza virus structural proteins, so that VLPs are assembled within the cells after expression of the influenza virus structural proteins: and co-transfecting, co-infecting or co-transforming the host cell with a recombinant DNA molecule which in terms of influenza virus proteins encodes only the influenza nucleocapsid protein (NP), so that NP is co-localized with the M1 structural protein, and
   (iv) purifying the VLPs from the culture supernatant.

7. A method of production of influenza virus-like particles (VLPs), said method consisting of the steps of:
   (i) constructing a recombinant DNA molecule which in terms of influenza virus proteins encodes only the influenza virus matrix structural protein (M1);
   (ii) constructing one or more recombinant DNA molecules which each encode at least one of but no more than all of the influenza virus structural proteins selected from the group consisting of hemagglutinin (HA), neuraminidase (NA) and the spliced product of M1mRNA (2);
   (iii) transfecting, infecting or otherwise transforming a suitable host cell with the recombinant DNA molecules referred to under (i) and with the recombinant DNA molecules referred to under (ii), culturing the host cell under conditions which permit the expression of said influenza virus structural proteins, so that VLPs are assembled within the cells after expression of the influenza virus structural proteins; and co-transfecting, co-infecting or co-transforming the host cell with a recombinant DNA molecule which encodes only a moiety not produced by influenza virus, so that the non-influenza moiety is encapsulated within the VLPs or is incorporated into the surface of the VLPs, and
   (iv) purifying the VLPs from the culture supernatant.

* * * * *

SEQUENCE LISTING

<160> NUMBER OF SEQ ID NOS: 11

<210> SEQ ID NO 1
<211> LENGTH: 71
<212> TYPE: PRT
<213> ORGANISM: Artificial Sequence
<220> FEATURE:
<223> OTHER INFORMATION: Description of Artificial Sequence:Chimera of
      portions of Vesicular Stomatitis Virus G protein
      and influenza HA protein

<400> SEQUENCE: 1

Gly Glu Thr Leu Phe Phe Gly Asp Thr Gly Leu Ser Lys Asn Pro Ile
 1               5                  10                  15

Glu Phe Val Glu Gly Trp Phe Ser Ser Trp Lys Ser Lys Ser Gly Tyr
            20                  25                  30

Lys Asp Trp Ile Leu Trp Ile Ser Phe Ala Ile Ser Cys Phe Leu Leu
        35                  40                  45

Cys Val Val Leu Leu Gly Phe Ile Met Trp Ala Cys Gln Lys Gly Asn
    50                  55                  60

Ile Arg Cys Asn Ile Cys Ile
65                  70

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence:Amino acids
      1-42 of human amyloid peptide protein

<400> SEQUENCE: 2

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence:Amino acids
      1-28 of human amyloid peptide protein

<400> SEQUENCE: 3

Asp Ala Glu Phe Arg His Asp Ser Gly Tyr Glu Val His His Gln Lys
 1               5                  10                  15

Leu Val Phe Phe Ala Glu Asp Val Gly Ser Asn Lys
            20                  25

<210> SEQ ID NO 4
<211> LENGTH: 39
<212> TYPE: DNA
<213> ORGANISM: Artificial Sequence
<220> FEATURE:

<223> OTHER INFORMATION: Description of Artificial Sequence:Primer

<400> SEQUENCE: 4
gtttaaacgc ggccgccgta tttataggtt tttttatta        39

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 5
ttttattact agtcccgggg atctgtgatt gtaaat        36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:Primer

<400> SEQUENCE: 6
aagagctcgc tagcgtattt ataggttttt ttatta        36

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence:Primer

<400> SEQUENCE: 7
acaatcacag atccccggga ctagtaataa aacctaga        38

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 8
gtttaaacgc ggccgccg        18

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:Primer

<400> SEQUENCE: 9
aagagctcgc tagcgta        17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:Primer

<400> SEQUENCE: 10
aacagagatc gatctgt        17

-continued

```
<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:Primer

<400> SEQUENCE: 11
cataaaaatt aaaaattaaa atataattaa gg                                     32
```